United States Patent [19]

Markley et al.

[11] Patent Number: 4,983,211
[45] Date of Patent: Jan. 8, 1991

[54] SUBSTITUTED CYCLOHEXANEDIONES AND THEIR HERBICIDAL USE

[75] Inventors: Lowell D. Markley; Christopher T. Hamilton, both of Midland, Mich.; Beth A. Swisher, Fairfield, Calif.; Jacob Secor, Midland, Mich.

[73] Assignee: DowElanco, Indianapolis, Ind.

[21] Appl. No.: 503,342

[22] Filed: Mar. 30, 1990

[51] Int. Cl.$^5$ .................. A01N 43/00; A01N 43/40; C07D 213/62; C07D 239/32

[52] U.S. Cl. ........................................ 71/94; 71/92; 544/239; 544/240; 544/241; 544/301; 544/311; 544/312; 544/316; 544/317; 544/408; 546/294; 546/295; 546/296; 546/300

[58] Field of Search ............... 546/294, 295, 296, 300; 544/239, 240, 241, 301, 311, 312, 316, 317, 408; 71/94, 92

[56] References Cited

U.S. PATENT DOCUMENTS

| | | | |
|---|---|---|---|
| 4,555,263 | 11/1985 | Serban et al. | 71/98 |
| 4,623,381 | 11/1986 | Jahn et al. | 546/294 |
| 4,631,081 | 12/1986 | Watson et al. | 71/94 |
| 4,680,400 | 7/1987 | Bird et al. | 546/141 |

*Primary Examiner*—Robert W. Ramsuer
*Assistant Examiner*—J. Richter
*Attorney, Agent, or Firm*—S. Preston Jones; Ronald G. Brookens

[57] ABSTRACT

The present disclosure is directed to substituted cyclohexanedione compounds, the preparation of said compounds, compositions containing said compounds and the use of said compositions in the selective pre- and postemergent kill and control of grassy weeds in the presence of various crop plants.

24 Claims, No Drawings

SUBSTITUTED CYCLOHEXANEDIONES AND THEIR HERBICIDAL USE

FIELD OF THE INVENTION

The present invention is directed to substituted cyclohexanedione compounds, compositions containing said compounds and the use of said compositions in the selective pre- and postemergent kill and control of grassy weeds.

SUMMARY OF THE INVENTION

The present invention is directed to cyclohexanedione compounds corresponding to the formula

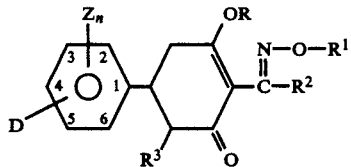

Wherein in this and in subsequent formula depictions, D is a group corresponding to one of the formulae,

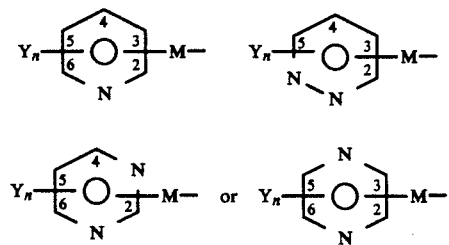

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen, $C_1$-$C_4$ alkyl or $C_1$-$C_4$ alkoxycarbonyl;

each Z independently represents hydrogen, halo, $C_1$-$C_4$ alkyl, $C_1$-$C_4$ alkoxy or —$CF_3$;

M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl; and n represents the integer 0, 1, 2 or 3;

and the herbicidally acceptable organic and inorganic salts thereof.

In addition, the present invention is directed to compositions containing the compounds of Formula I, as an active ingredient therein, and to methods of using said compositions in the selective pre- and postemergent kill and control of grassy weeds, especially in the presence of crop plants such as those hereinafter set forth. The present invention is also directed to a method of preparing the compounds of Formula I.

In the present specification and claims, the term "halo" designates the halogen groups bromo, chloro, fluoro and iodo.

In the present specification and claims, the term "$C_1$-$C_4$ alkyl" designates alkyl groups of 1 to 4 carbon atoms such as, for example, methyl, ethyl, n-propyl, i-propyl, n-butyl, i-butyl, sec.-butyl or t-butyl.

In the present specification and claims, the term "$C_1$-$C_4$ alkoxy" designates alkoxy groups of 1 to 4 carbon atoms such as, for example, methoxy, ethoxy, n-propoxy, i-propoxy, n-butoxy, i-butoxy, sec.-butoxy or t-butoxy.

In the present specification and claims, the term "$C_1$-$C_4$ fluoroalkyl" designates alkyl groups of 1 to 4 carbon atoms substituted with from 1 fluoro atom up to perfluoro substitution.

In the present specification and claims, the term "$C_2$-$C_4$ alkenyl" designates alkenyl groups of 2 to 4 carbon atoms such as, for example, vinyl, allyl, 2-butenyl, 3-butenyl or methallyl.

In the present specification and claims, the term "$C_2$-$C_4$ haloalkenyl" designates alkenyl groups of 2 to 4 carbon atoms substituted with from 1 halo atom up to perhalo substitution.

In the present specification and claims, the term "$C_3$-$C_4$ alkynyl" designates alkynyl groups of 3 or 4 carbon atoms such as, for example, propargyl, 2-butynyl or 3-butynyl.

In the present specification and claims, the term "$C_3$-$C_4$ haloalkynyl" designates alkynyl groups of 3 or 4 carbon atoms substituted with from 1 halo atom up to perhalo substitution.

In the present specification and claims, the term "$C_1$-$C_4$ alkylthio", "$C_1$-$C_4$ alkylsulfinyl" and "$C_1$-$C_4$ alkylsulfonyl" designates alkylthio, alkylsulfinyl and alkylsulfinyl groups of 1 to 4 carbon atoms wherein alkyl is as defined above.

In the present specification and claims, the term "acyl" designates radicals of the formula $R^4$—C(O)— wherein $R^4$ represents $C_1$-$C_4$ alkyl, $C_1$-$C_4$ haloalkyl and phenyl.

The active ingredients of Formula I wherein R represents hydrogen constitutes a preferred embodiment. The active ingredients of Formula I wherein $R^1$ and $R^2$ each represent alkyl constitutes a more preferred embodiment. The active ingredients of Formula I wherein D represents pyridyl and Y represents alkylthio or alkylsulfonyl constitute a most preferred embodiment.

In the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows:

"steric hindrance. A characteristic of molecular structure in which the molecules have a spatial arrangement of their atoms such that a given reaction with another molecular is prevented or retarded in rate."

Sterically compatible may be further defined as reacting compounds having substituents whose physical bulk does not require confinement within volumes insufficient for the exercise of their normal behavior as discussed in *Organic Chemistry* by D. J. Cram and G. Hammond, 2nd edition, McGraw-Hill Book Company, N.Y., page 215 (1964).

The cyclohexanediones of the present invention, may exist in either form or in mixtures of the isomeric forms set forth below:

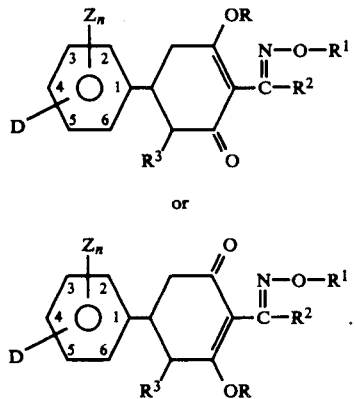

The cyclohexanediones of the present invention, when R is hydrogen, can exist in any of the four tautomeric forms set forth hereinbelow:

wherein J in this and succeeding formula represents a moiety corresponding to the formula:

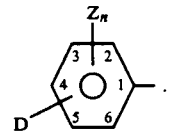

The compounds of the present invention are generally low melting crystalline solids at ambient temperatures which are soluble in many organic solvents.

Representative compounds which correspond to Formula I (Compounds of Formulas II through VI) include the compounds set forth below in Tables I through V.

In the following Tables the middle ring is listed as the prime "'" ring.

TABLE I

| Y | M | Z | R | $R^1$ | $R^2$ | $R^3$ |
|---|---|---|---|---|---|---|
| —H | 2,3'-O | —H | —H | ethyl | ethyl | —H |
| 5-CH$_3$ | 2,3'-O | —H | —H | ethyl | ethyl | —H |
| 5-Br | 2,3'-O | —H | —H | ethyl | ethyl | —H |
| 5-CN | 2,3'-O | —H | —H | ethyl | ethyl | —H |
| 5-Cl | 2,3'-O | —H | —H | ethyl | ethyl | —H |
| 5-CH$_3$SO$_2$ | 2,3'-O | —H | —H | ethyl | ethyl | —H |
| 3-F, 5-CF$_3$ | 2,4'-O | —H | —H | ethyl | n-propyl | —H |
| 3-F, 5-CF$_3$ | 2,4'-O | —H | —H | ethyl | ethyl | —H |
| 3-F, 5-CF$_3$ | 2,4'-O | 2',6'-(CH$_3$)$_2$ | —H | ethyl | ethyl | —H |
| 3-Cl, 5-CF$_3$ | 2,4'-O | —H | —H | ethyl | ethyl | —H |
| 3-Cl, 5-CF$_3$ | 2,4'-O | —H | —H | allyl | ethyl | —H |
| 3-F, 5-CF$_3$ | 2,3'-O | —H | —H | ethyl | ethyl | —H |
| 3-F, 5-CF$_3$ | 2,3'-O | —H | —H | ethyl | n-propyl | —H |
| 3-Cl, 5-CF$_3$ | 2,3'-O | —H | —H | ethyl | methyl | —H |
| 3-Cl, 5-CF$_3$ | 2,3'-O | —H | —H | ethyl | ethyl | —H |
| 3,5-Cl$_2$ | 2,3'-O | —H | —H | ethyl | n-propyl | —H |
| 3,5-Cl$_2$ | 2,4'-O | —H | —H | ethyl | ethyl | —CO$_2$Et |
| 5-CF$_3$ | 2,3'-O | —H | —H | ethyl | ethyl | —H |
| 6-CF$_3$ | 2,3'-O | —H | —H | ethyl | ethyl | —CO$_2$Et |
| 3-F, 5-CF$_3$ | 2,3'-O | 4'-Br | —H | ethyl | ethyl | —H |
| 3-F, 5-CF$_3$ | 2,3'-O | 4'CH$_3$O— | —H | ethyl | ethyl | —H |
| 6-CF$_3$ | 2,4'-O | —H | —H | ethyl | ethyl | —H |
| 4-CF$_3$ | 2,3'-O | —H | —H | ethyl | ethyl | —H |
| 3-CF$_3$ | 2,3'-O | —H | —H | ethyl | ethyl | —H |
| 5-CF$_3$ | 2,3'-O | —H | —H | ethyl | ethyl | —H |
| 3-F, 5-CF$_3$ | 2,3'-O | 4'-F | —H | ethyl | ethyl | —H |

TABLE I-continued

Structure II: Pyridine ring (Y_n substituted) — M — phenyl ring (Z_n substituted) — cyclohexenone with OR, N—O—R¹, C—R², and R³ substituents.

| Y | M | Z | R | R¹ | R² | R³ |
|---|---|---|---|---|---|---|
| 6-Cl, 5-CF₃ | 2,3'-O | —H | —H | ethyl | ethyl | —H |
| 6-Cl, 3-CF₃ | 2,3'-O | —H | —H | ethyl | ethyl | —H |
| 5-CH₃SO₂ | 2,3'-O | —H | —H | ethyl | ethyl | —H |
| 5-CH₃SO₂ | 2,3'-O | —H | —H | ethyl | n-propyl | —H |
| 5-CH₃SO₂ | 2,3'-O | —H | —H | trans-CH₂CH=CHCl | ethyl | —H |
| 5-CH₃SO₂ | 2-3'-O | —H | —H | allyl | ethyl | —H |
| 6-CH₃SO₂ | 2-3'-O | —H | —H | allyl | ethyl | —H |
| 6-CH₃S | 2-3'-O | —H | —H | ethyl | ethyl | —H |
| 5-CH₃SO₂ | 2-3'-O | —H | —H | ethyl | ethyl | —CO₂Et |
| 5-CH₃S | 2-3'-O | —H | —H | ethyl | ethyl | —H |
| 5-CH₃SO | 2-3'-O | —H | —H | ethyl | ethyl | —H |
| 5-C₂H₅SO | 2-3'-O | —H | —H | ethyl | ethyl | —H |
| 5-C₂H₅SO₂ | 2,3'-O | —H | —H | ethyl | ethyl | —H |
| 6-C₂H₅SO₂ | 2,3'-O | —H | —H | ethyl | ethyl | —H |
| 6-C₂H₅S | 2,3'-O | —H | —H | ethyl | ethyl | —H |
| 3-F, 5-CF₃ | 2,4'-O | —H | —H | allyl | n-propyl | —H |
| 5-Br | 2,3'-O | —H | —H | ethyl | ethyl | —H |
| 6-(CH₃)CHS | 2,3'-O | —H | —H | ethyl | ethyl | —H |
| 5-(CH₃)CHS | 2,3'-O | —H | —H | ethyl | ethyl | —H |
| 5-(CH₃)CHSO | 2,3'-O | —H | —H | ethyl | ethyl | —CO₂Et |
| 5-(CH₃)CHSO₂ | 2,3'-O | —H | —H | ethyl | ethyl | —H |
| 5-CH₃SO₂ | 2,4'-O | —H | —H | ethyl | ethyl | —H |
| 5-CH₃ | 2,3'-O | —H | —H | ethyl | ethyl | —H |
| 4-CH₃S | 2-3'-O | —H | —H | ethyl | ethyl | —H |
| 5-CH₃S, 6-CN | 2-3'-O | —H | —H | ethyl | ethyl | —H |
| 4-CH₃SO₂ | 2,3'-O | —H | —H | ethyl | ethyl | —H |
| —H | 2,3'-S | 2,6-Cl₂ | CH₃SO₂— | Cl—CH₃ | CH₃SCH₂ | —CO₂-n-Bu |
| 4-CH₃SO₂ | 2,3'-SO | 2,6-(CH₃)₂ | vinyl | Cl—CH₂— | n-propyl | H |

TABLE II

Structure III: Pyridazine ring (Y_n substituted) — M — phenyl ring (Z_n substituted) — cyclohexenone with OR, N—O—R¹, C—R², and R³ substituents.

| Y | M | Z | R | R¹ | R² | R³ |
|---|---|---|---|---|---|---|
| —H | 2,3'-O | —H | —H | ethyl | ethyl | —H |
| 5-CH₃ | 2,3'-O | —H | —H | ethyl | ethyl | —H |
| 5-Br | 2,3'-O | —H | —H | ethyl | ethyl | —H |
| 5-CN | 2,3'-O | —H | —H | ethyl | ethyl | —H |
| 5-Cl | 2,3'-O | —H | —H | ethyl | ethyl | —H |
| 5-CH₃SO₂ | 2,3'-O | —H | —H | ethyl | ethyl | —H |
| 3-Cl, 5-CF₃ | 2,4'-O | —H | —H | ethyl | ethyl | —H |
| 5-CF₃ | 3,4'-O | —H | —H | ethyl | ethyl | —H |
| 3-F, 5-CF₃ | 2,4'-O | —H | —H | n-propyl | ethyl | —H |
| 3-Cl, 5-CF₃ | 2,4'-O | —H | —H | allyl | ethyl | —H |
| 3-F, 5-CH₃SO₂ | 4,3'-O | 2,6-(CH₃)₂ | —H | ethyl | ethyl | —H |
| 3,5-Cl₂ | 2,3'-O | 2,6-Cl₂ | vinyl | ethinyl | n-propyl | —Cl |
| 3-Cl, 5-CF₃ | 2,3'-O | —H | —H | ethyl | methyl | —H |
| 3-F, 5-CF₃ | 2,3'-S | —H | —H | ethyl | ethyl | —H |
| 3-Cl, 5-CF₃ | 2,3'-S | —H | —H | ethyl | ethyl | —H |
| 3-F, 5-CF₃ | 2,3'-O | —H | —H | ethyl | ethyl | —H |
| 3-F, 5-CF₃ | 2,4'-O | —H | —H | ethyl | n-propyl | —H |
| 3-F, 5-CF₃ | 2,3'-O | —H | —H | ethyl | ethyl | —H |
| 3-Cl, 5-CF₃ | 2,3'-S | —H | —H | ethyl | ethyl | —H |
| 3-CH₃S | 2,4'-S | 3-methoxy | CH₃SO₂— | Cl—CH₂— | vinyl | —CN |

TABLE III

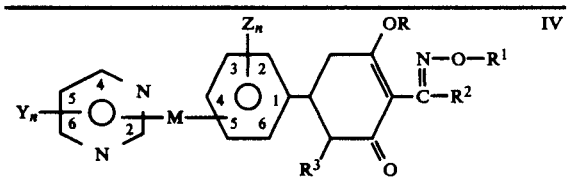

| Y | M | Z | R | R¹ | R² | R³ |
|---|---|---|---|---|---|---|
| —H | 2,3'-O | —H | —H | ethyl | ethyl | —H |
| 5-CH₃ | 2,3'-O | —H | —H | ethyl | ethyl | —H |
| 5-Br | 2,3'-O | —H | —H | ethyl | ethyl | —H |
| 5-CN | 2,3'-O | —H | —H | ethyl | ethyl | —H |
| 5-Cl | 2,3'-O | —H | —H | ethyl | ethyl | —H |
| 5-CH₃SO₂ | 2,3'-O | —H | —H | ethyl | ethyl | —H |
| 4,6-(CH₃)₂ | 2,3'-O | —H | —H | ethyl | ethyl | —H |
| 4,6-(CH₃O)₂ | 2,3'-O | —H | —H | ethyl | ethyl | —H |
| 4-SCH₃, 5-CH₃ | 2,3'-O | —H | —H | ethyl | ethyl | —H |
| 4-SCH₃, 5-F | 2,3'-O | —H | —H | ethyl | ethyl | —H |
| 2-CH₃SO₂ | 4,3'-O | —H | —H | ethyl | ethyl | —H |
| 2-CH₃S | 4,3'-O | —H | —H | ethyl | ethyl | —H |
| 4-CH₃SO₂, 5-CH₃ | 2,3'-O | —H | —H | ethyl | ethyl | —H |
| 5-CF₃ | 2,3'-O | —H | —H | ethyl | methyl | —H |
| 5-CF₃ | 2,3'-S | —H | —H | ethinyl | ethyl | —H |
| 5-CF₃ | 2,3'-S | —H | —H | allyl | ethyl | —H |
| 5-CF₃ | 2,4'-O | —H | —H | ethyl | ethyl | —Cl |
| 5-CF₃ | 2,4'-S | —H | —H | ethyl | n-propyl | —H |

TABLE IV

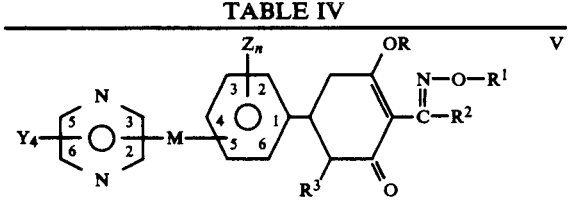

| Y | M | Z | R | R¹ | R² | R³ |
|---|---|---|---|---|---|---|
| —H | 2,3'-O | —H | —H | ethyl | ethyl | —H |
| 5-CH₃ | 2,3'-O | —H | —H | ethyl | ethyl | —H |
| 5-Br | 2,3'-O | —H | —H | ethyl | ethyl | —H |
| 5-CN | 2,3'-O | —H | —H | ethyl | ethyl | —H |
| 5-Cl | 2,3'-O | —H | —H | ethyl | ethyl | —H |
| 5-CH₃SO₂ | 2,3'-O | —H | —H | ethyl | ethyl | —H |
| 5-CF₃ | 2,3'-O | —H | —H | ethyl | methyl | —H |
| 5-CF₃ | 2,3'-S | —H | —H | ethinyl | ethyl | —H |
| 5-CF₃ | 2,3'-S | —H | —H | allyl | ethyl | —H |
| 5-CF₃ | 2,4'-O | —H | —H | ethyl | ethyl | —Cl |
| 5-CF₃ | 2,4'-S | —H | —H | ethyl | n-propyl | —H |

In the preparation of the compounds of the present invention, the amounts of the reactants to be employed is not critical. In most cases it is preferred to employ substantially equimolar amounts of the reactants. Depending upon the specific type of reaction taking place, it may be beneficial that a given one of the reactants be present in a slight excess to obtain the highest yields of the desired product.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an equivalent solvent, the use of an excess of one of the reactants, the use of a catalyst, the use of high temperature and/or pressure equipment, high speed mixing and other such conventional changes are within the scope of this invention.

The desired product can be separated from the reaction product of the above preparative procedures employing conventional separator procedures known to those skilled in the art including steps such as, for example, solvent extraction, filtration, water washing, column chromatography, neutralization, acidification, crystallization and distillation.

The compounds corresponding to Formula I of the present invention, wherein R is hydrogen, can be prepared by the reaction of an appropriate ketone reactant, corresponding to Formula VI:

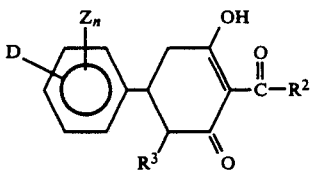

wherein D, Z, R² and R³ are hereinbefore defined, with an excess of an appropriate alkoxyamine reactant corresponding to the formula R¹ONH₂ (wherein R¹ is as hereinbefore defined) or an inorganic salt thereof and from about 1-2 moles of a base. This reaction can be conducted at temperatures of from about 0° to about 100° C. in the presence of a solvent.

Representative solvents include, for example, dimethyl sulfoxide, $C_1$–$C_4$ alkanols, hydrocarbons, cyclic ethers, halohydrocarbons, and the like, with the $C_1$–$C_4$ alkanols being preferred.

Representative bases include, for example, the carbonates, acetates, alcoholates and hydroxides of the alkali and alkaline earth metals, in particular, sodium and potassium, and organic bases, such as pyridine or tertiary amines, with anhydrous sodium acetate being preferred.

The reaction time can extent for a time of from a few minutes up to 24 hours or more, depending upon the specific reactants and reaction temperature. The product can be recovered employing conventional separatory techniques.

The herbicidally acceptable organic and inorganic salts of the compounds of Formula I can be prepared from said compounds of Formula I employing conventional procedures. The salts are conveniently obtained by mixing an appropriate organic or inorganic base with a compound of Formula I where R is hydrogen, if necessary, in an inert solvent; distilling off the solvent and recrystallizing the residue as necessary.

Representative solvents include, for example, dimethyl sulfoxide, $C_1$–$C_4$ alkanols, hydrocarbons, cyclic ethers, halohydrocarbons, and the like, with the $C_1$–$C_4$ alkanols being preferred.

Representative bases include, for example, the carbonates, acetates, alcoholates and hydroxides of the alkali and alkaline earth metals, in particular, sodium and potassium, and organic bases, such as pyridine or tertiary amines, with anhydrous sodium acetate being preferred. For ease of formulation, these salts are prepared by neutralization of the above compound of Formula I in an equimolar amount of the base. Other metal salts such as, for example, the manganese, copper, zinc and iron salts can be prepared from the alkali metal salts employing conventional procedures. The ammonium and phosphonium salts can also be obtained employing conventional procedures.

The compounds corresponding to Formula I, wherein R is other than hydrogen, can be prepared by reacting a compound Formula I, wherein R is hydrogen with a compound of the formula $R^a$-L wherein $R^a$ represents $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl and L is a leaving group such as, for example, chloride, bromide, iodide, nitrate, sulfate, methyl sulfate, ethyl sulfate, tetrafluoroborate, hexafluorophosphate, methanesulfonate, fluorosulfonate and trifluoromethanesulfonate.

The above reaction can be carried out employing the appropriate conventional etherification, acylation or sulfonylation reaction procedures such as taught in U.S. Pat. Nos. 4,631,081 and 4,680,400.

The compounds corresponding to Formula VI can be prepared by the reaction of an appropriate reactant corresponding to Formula VII

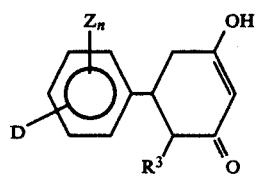

with an excess of an anhydride corresponding to the formula ($R^2$—C=O)$_2$O (wherein $R^2$ is as hereinbefore defined) in the presence of a catalytic amount of a catalyst such as, for example, 4-dimethylaminopyridine or imidazole and an aprotic solvent, such as, for example, benzene, chloroform and toluene and in the presence of at least a stoichiometric amount of a base such as, for example, pyridine or dimethylaminopyridine.

This reaction is usually carried out by stirring the mixture at ambient temperatures for a period of from about 10 minutes up to about 4 hours and then stirring the mixture under reflux conditions for up to about six hours. The mixture is cooled to room temperature, diluted with a solvent such as, for example, diethyl ether and washed with water, followed by a wash with 1N HCl and then dried. The solvent is removed and the product can be purified, if desired, employing conventional techniques.

The compounds corresponding to Formula VI can also be prepared by the reaction of an appropriate compound corresponding to one of the formulae set forth below as D-1,

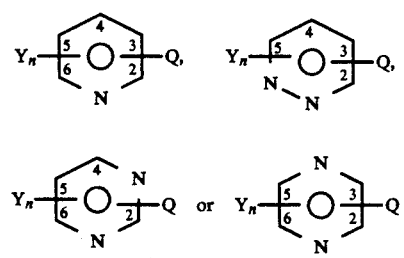

wherein Q represents halo or methylsulfonyl, with an appropriate cyclohex-2-en-1-one compound corresponding to Formula VIII

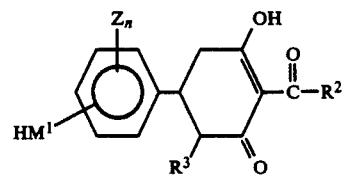

wherein $M^1$ is oxygen or sulfur. This reaction can be conducted, with agitation, at temperatures of from about room temperature up to about 140° C. for times of from about 10 minutes up to about 24 hours or more, in the presence of a solvent such as, for example, methyl sulfoxide and a basic material such as, for example, potassium t-butoxide or potassium carbonate. The product can be recovered employing conventional techniques.

The compounds of Formula VII which are exemplified by the formula

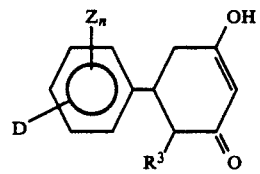

can be prepared by the reaction of an appropriate compound corresponding to D-1, with an appropriate cyclohex-2-en-1-one compound corresponding to Formula IX

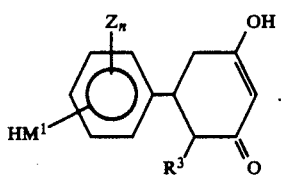

This reaction can be conducted, with agitation, at temperatures of from about room temperature up to about 140° C. for times of from about 10 minutes up to about 24 hours or more, in the presence of a solvent such as, for example, methyl sulfoxide and a basic material such as, for example, potassium t-butoxide. The product can be recovered employing conventional techniques.

If it is desired that $R^3$ in the compound of Formula VIII or IX is hydrogen, a mixture of the compound, prepared as above, wherein $R^3$ is alkoxycarbonyl, and 1N sodium hydroxide can be heated at a temperature of from about 50° to about 85° C. for from about 1 up to about 8 hours. The mixture is cooled to room temperature, filtered, the filtrate diluted with water and acidified with a mineral acid and allowed to stand whereby the desired product separates out. The product, if desired, can be further purified employing conventional procedures.

If it is desired that M in the compound of Formulae VI and VII, as defined for "D" in Formula I, is "SO" or "SO$_2$", the corresponding compound wherein M is "S", as prepared hereinabove, is treated with conventional oxidizing materials such as m-chloroperbenzoic acid or hydrogen peroxide in acetic acid and the like using conventional oxidation procedures.

The compounds corresponding to Formula IX wherein $M^1$ is O and which are exemplified by Formula Xa

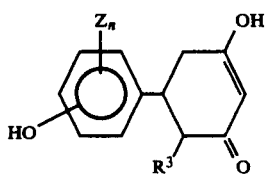

can also be prepared by hydrogenating an appropriate compound corresponding to Formula X and which is exemplified by the formula

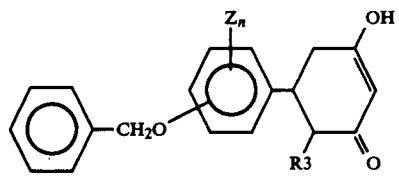

In carrying out this reaction, the compound is hydrogenated at room temperature, in a solvent and in the presence of a hydrogenation catalyst, under hydrogen partial pressures of from about 2 to about 5 atmospheres. The reaction mixture is then filtered, diluted with water and solvent extracted, and the solvent removed to precipitate the desired product.

The compounds corresponding to Formula IX, wherein $M^1$ is sulfur and which are exemplified by Formula IXb

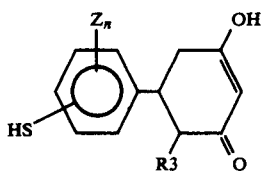

can be prepared using the Pummerer rearrangement reaction wherein an appropriate compound corresponding to Formula IXb-1

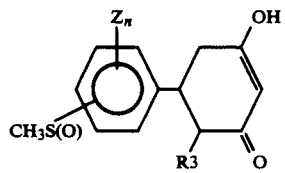

(which is prepared by the oxidation of a compound corresponding to Formula IXb-2; prepared as taught in U.S. Pat. No. 4,555,263

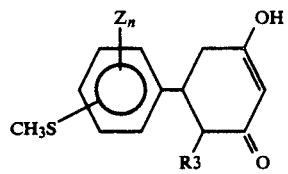

using conventional oxidation procedures with oxidation agents such as, for example, hydrogen peroxide in acetic acid).

In carrying out this reaction, the appropriate compound of Formula IXb-1, at a temperature of about 0° to about 10° C. is slowly added to trifluoroacetic anhydride and the mixture stirred at ambient temperature for from about 1 to about 6 hours. The excess trifluoroacetic anhydride is removed and the residue dissolved in dilute base and this solution stirred at ambient temperature for from about 10 to about 24 hours. The alkaline product can be converted to the H+ form using conventional treatment with an acid.

If it is desired that $R^3$ in the compounds of Formula IXa and b is hydrogen, the compound prepared as above, can be converted to the desired form in the same manner as set forth hereinabove for other such compound conversions.

The compounds corresponding to Formula IX wherein $M^1$ is O and $R^3$ is alkoxycarbonyl and which are exemplified by Formula IXc

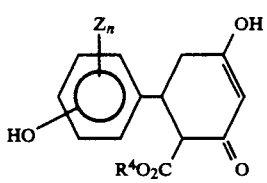

wherein $R^4$ is $C_1$-$C_4$ alkyl can also be prepared by reacting 1-(3- or 4-hydroxyphenyl)-but-1-en-3-one (prepared according to the procedure described by Marrion et al, J. Biochem. vol. 45, 533 (1949)) with the anion of dialkylmalonates.

In carrying out this reaction, the butene-3-one reactant, in an alkanol, is admixed with a solution prepared by mixing equimolar amounts of a solution of a dialkyl malonate in an alkanol and a solution of fresh sodium metal dissolved in an alkanol. This mixture is stirred at a temperature of from room temperature up to the reflux temperature of the mixture for about 24 hours or more, depending on the specific reactants, and then concentrated HCl is added which converts the intermediate sodium salt of the cyclohex-2-en-1-one product to the desired acid form of Formula IXc. If, due to solubility differences, the intermediate sodium salt of the desired product precipitates, it is usually redissolved by the addition of water prior to treatment with HCl.

The compounds corresponding to Formula X wherein $R^3$ is alkoxycarbonyl and which are exemplified by the formula

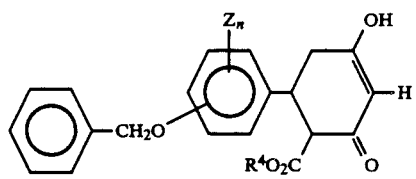

can be prepared by admixing an appropriate compound corresponding to the formula

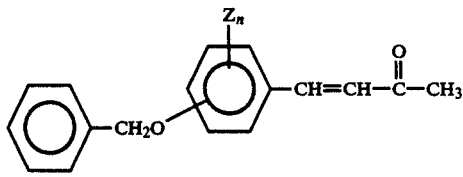

XI with a solution prepared by treating at room temperature, a solution of a sodium alkoxide with a solution of dialkyl malonate in an alkanol solvent. After stirring the mixture for a period of from about 12 to about 48 hours or more, the mixture is then diluted with water, acidified with a mineral acid and extracted with a solvent such as, for example, ethyl acetate or methylene chloride. The organic layer is dried, filtered and concentrated by solvent removal. The mixture is cooled to precipitate the product.

If it is desired that $R^3$ in the compound of Formula XI is hydrogen, the compound prepared as above can be converted to the desired form in the same manner as set forth hereinabove.

The compounds corresponding to Formula XI can be prepared by treating, with agitation, a solution of an appropriate benzyloxybenzaldehyde corresponding to Formula XII

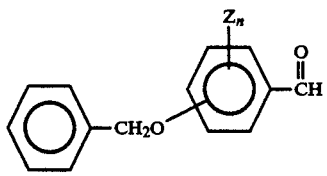

XII in acetone and water with a catalytic amount of a base, for example, sodium hydroxide. The crude product is recovered by filtration and purified by conventional solvent recrystallization.

The compounds corresponding to Formula VIII wherein $M^1$ is S and which correspond to the formula

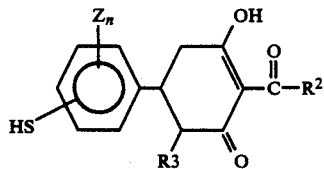

VIIIa can be prepared using the Pummerer rearrangement reaction starting with an appropriate cyclohex-2-en-1-one compound corresponding to Formula XIII

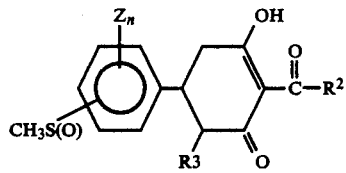

XIII

In carrying out this reaction, the appropriate cyclohex-2-en-1-one of Formula XIII, at a temperature of about 0° to about 10° C., is slowly added to trifluoroacetic anhydride and the mixture stirred at ambient temperature for from about 1 to about 6 hours. The excess trifluoroacetic anhydride is removed and the residue dissolved in dilute base (such as one of those set forth hereinabove) and this solution stirred at ambient temperatue for from about 10 to about 24 hours. The alkaline product can be converted to the H+ form using conventional treatment with an acid.

The compounds corresponding to Formula XIII can be prepared by the oxidation of an appropriate cyclohex-2-en-1-one compound corresponding to Formula XIV.

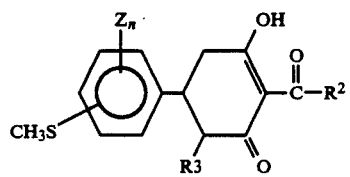

XIV using conventional oxidation techniques such as, for example, treatment with a mixture of glacial acetic acid and hydrogen peroxide.

The compounds corresponding to Formula XIV are known and can be prepared as taught in U.S. Pat. No. 4,555,263.

The compounds corresponding to Formula VII wherein $R^3$ is alkoxycarbonyl can also be prepared by admixing an appropriate buten-3-one compound corresponding to Formula XVI

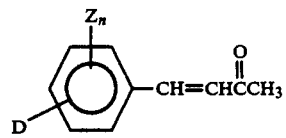

XV in an alkanol, with a solution prepared by mixing equimolar amounts of a solution of dialkyl malonate in an alkanol and a solution of fresh sodium metal dissolved in an alkanol. This mixture is stirred at room temperature for about 24 hours or more and then concentrated HCl is added which converts the intermediate sodium salt of the cyclohex-2-en-1-one product to the desired acid form of Formula VII.

The above compounds corresponding to Formula XVI can be prepared by reacting an appropriate benzaldehyde reactant corresponding to Formula XVI

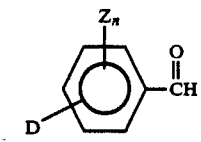

XVI with agitation, with acetone in water and a base. The crude product is recovered by filtration and purified by conventional solvent recrystallization.

The above compounds corresponding to Formula XVII can be prepared by in a procedure wherein a mixture comprising an appropriate hydroxybenzaldehyde reactant corresponding to Formula XVII

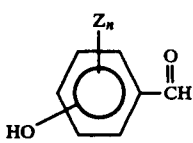

is reacted with an appropriate compound corresponding to one of the formulae set forth below as D-1

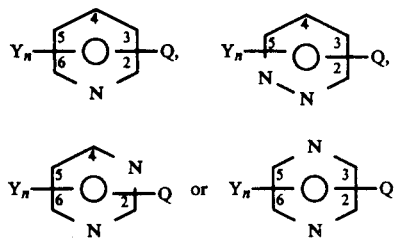

This reaction can be conducted, with agitation, at temperatures of from about room temperature up to the reflux temperature of the mixture for times of from about 3 up to about 24 hours or more, in the presence of a basic material such as, for example, powdered potassium carbonate. The process can, if desired, be conducted in the presence of a solvent such as, for example, acetonitrile, dimethylsulfoxide, diglyme or dimethylformamide. The product can be recovered employing conventional techniques.

An alternative preparation for the compounds of Formula XVII involves the reaction of a benzaldehyde of Formula XVIII

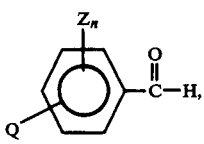

wherein Q is as hereinbefore defined, with a compound corresponding to one of the formulae set forth below as D-2

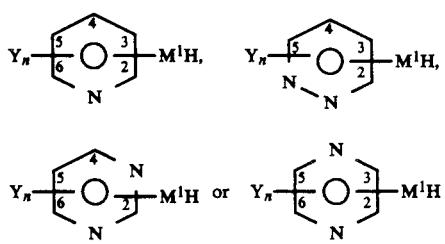

wherein $M^1$ is as hereinbefore defined. This reaction can be conducted, with agitation, at temperatures of from about room temperature up to about 140° C. for times of from about 10 minutes up to about 24 hours or more, in the presence of a solvent such as, for example, methyl sulfoxide and a basic material such as, for example, potassium t-butoxide or potassium carbonate. The product can be recovered employing conventional techniques.

The compounds corresponding to Formula VII wherein $M^1$ is 0 can be prepared by reducing a cyclohex-2-en-1-one compound corresponding to Formula XIX

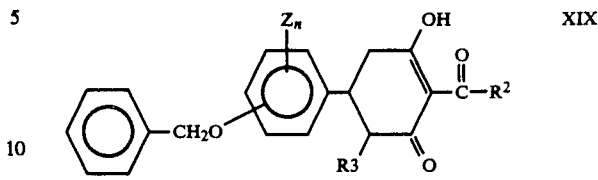

In carrying out this reaction, a mixture of cyclohexene and a catalyst such as palladium hydroxide on carbon (Pearlman's catalyst) is added to a solution comprising an appropriate cyclohex-2-en-1-one compound of Formula XX in a mixture of ethyl acetate and absolute ethanol and the mixture heated at reflux for from about 2 to about 10 hours. The mixture is cooled and filtered and the filtrate evaporated leaving the product as a crude residue. If desired, the product can be purified by conventional treatments such as solvent refining.

If it is desired that $R^3$ in the compound of Formula XX is hydrogen, a mixture of the compound, prepared as above is converted to the desired form in the same manner as set forth hereinabove.

The compounds corresponding to Formula VII wherein $M^1$ is 0 and $R^3$ is hydrogen can also be prepared by heating a solution of a cyclohex-2-en-1-one compound corresponding to Formula XX

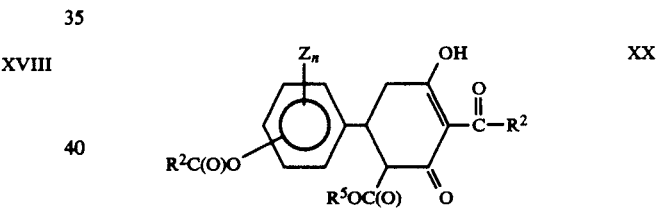

in excess 1N sodium hydroxide at a temperature of from about 50° to about 85° C. for from about 1 up to about 24 hours. The mixture is then cooled to room temperature, filtered, the filtrate diluted with water and acidified with a mineral acid and allowed to stand whereby the desired product separates out. The product, if desired, can be further purified employing conventional procedures.

The compounds corresponding to Formula XIX wherein $R^3$ is alkoxycarbonyl and which are exemplified by the formula

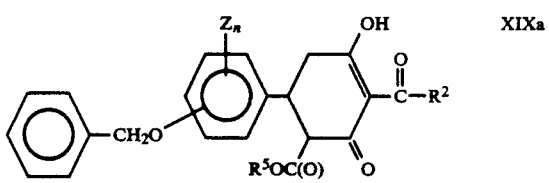

can be prepared by heating an appropriate cyclohex-2-en-1-one corresponding to the formula

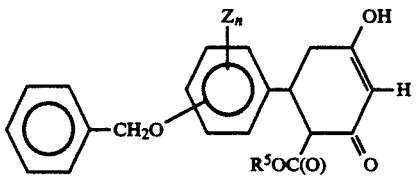

in a solvent such as, for example, chloroform or benzene which contains an appropriate alkanoic anhydride and a base such as, for example, pyridine or triethylamine and a catalyst such as, for example, 4-dimethylaminopyridine or imidazole at a temperature of from about 40° C. up to the reflux temperature of the mixture. After a heating period of from about 6 to about 24 hours, the mixture is cooled to room temperature and washed with 1N HCl and then with a saturated NaCl solution, dried and the solvent removed employing conventional separatory procedures. If desired, the product can be purified by conventional treatments such as solvent refining.

The compounds corresponding to Formula XX can be prepared by treating a solution of the cyclohex-2-en-1-one of Formula Xc which are exemplified by the formula

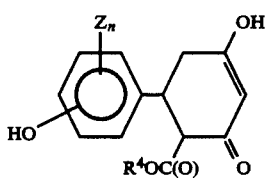

in a solvent such as, for example, benzene, toluene or chloroform with an appropriate alkanoic anhydride in the presence of a base such as, for example, pyridine or triethylamine and a catalyst such as, for example, 4-dimethylaminopyridine or imidazole at a temperature of from about room temperature up to the reflux temperature of the mixture. After a heating period of from about 1 to about 8 hours, the mixture is cooled to room temperature, diluted with a solvent such as, for example, diethyl ether and washed with 1N HCl and then with water, dried and the solvent removed employing conventional separatory procedures.

The following Examples illustrate the present invention and the manner by which it can be practiced, but as such, should not be construed as limitations upon the overall scope of the same.

EXAMPLE I 2-(1-(Ethoxyimino)propyl)-3-hydroxy-5-(4-(5-(trifluoromethyl)-3-fluoro-2-pyridyloxy)phenyl)cyclohex-2-en-1-one

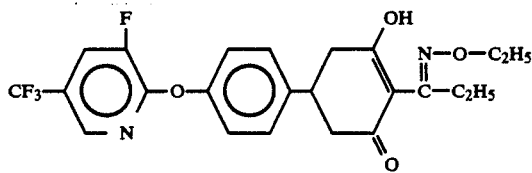

To a slurry of 5.0 g (0.0118 mol) of 3-hydroxy-5-(4-((5-trifluoromethyl)-3-fluoro-2-pyridyloxy)phenyl)-2-propionylcyclohex--2-en-1-one in 75 mL of 95 percent ethanol was added 1.21 g (0.0124 mol) of ethoxyamine hydrochloride and 1.02 g (0.0124 mol) of anhydrous sodium acetate. The mixture was stirred at ambient temperature for 23 hours with sodium chloride precipitating. The mixture was diluted with 200 mL of methylene chloride and 200 mL of water. The organic layer was separated in a separatory funnel and washed thoroughly with water and dried over sodium sulfate. The solvent was removed in vacuo leaving 5.4 g (98 percent of theoretical) of the above named compound, as the crude product. The above named title compound (melting at 82°–82.5° C.) was recovered in a yield of 3.8 g (69 percent of theoretical) after recrystallization of the crude product from hexane; $R_f$ —0.34 (silica gel, 20:80 acetone:hexane), $^1$H NMR: 67 1.14 (t, 3H, —CH$_2$CH$_3$), 1.30 (t, 3H, —OCH$_2$CH$_3$), 2.5–3.6 (m, 7H, ring protons and —CH$_2$CH$_3$), 4.1 (q, 2H, —OCH$_2$CH$_3$), 7.05–8.25 (m, 6H, ArH), 14.9 (s, 1H, —OH) (Compound 1).

| Analysis | percent | | |
|---|---|---|---|
| | C | H | N |
| Calc. for $C_{23}H_{22}F_4N_2O_4$ | 59.22 | 4.75 | 6.01 |
| Found | 59.08 | 4.74 | 5.86 |

EXAMPLE II 2-(1-(Ethoxyiminio)propyl)-3-hydroxy-5-(4-(5-(methylsulfonyl)-2-pyridyloxy)phenyl)cyclohex-2-en-1-one

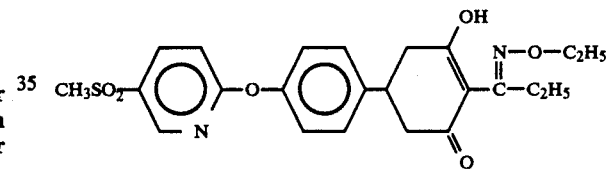

A solution of 1.5 g (3.6 mmol) of 2-propionyl-3-hydroxy-5-(4-(5-(methylsulfonyl)-2-pyridyloxy)-phenyl)cyclohex-2-en-1-one in 20 mL of dichloromethane and 25 mL of absolute ethanol was treated with 0.45 g (4.7 mmol) of ethoxyamine hydrochloride and 0.45 g (5.5 mmol) of sodium acetate. After stirring at ambient temperature for 24 hours, the reaction mixture was diluted with 100 mL of an aqueous NaCl solution and extracted thrice with 50 mL portions of dichloromethane. The solvent extracts were combined and dried over MgSO$_4$, filtered and the solvent removed by evaporation leaving a solid residue. Recrystallization of the residue from a 2:1 benzene-hexane mixture gave the above named product as a white solid in a yield of 1.4 g (85 percent of theoretical). The product melted at 171°–174° C.; $^1$H NMR (CDCl$_3$): δ1.08–1.45 (m, 6H, two —CH$_2$CH$_3$'s), 2.62–3.60 (m includes s at 3.08 for CH$_3$SO$_2$—, 10H, ring protons and —N═CCH$_2$CH$_3$), 7.05–7.45 (m, 5H, ArH's), 8.22 (dd, 1H, ArH), 8.75 (d, 1H, ArH) 15 (broad s, enol H) (Compound 2).

| Analysis | percent | | |
|---|---|---|---|
| | C | H | N |
| Calc. for $C_{23}H_{26}N_2O_6S$ | 60.20 | 5.72 | 6.11 |
| Found | 59.80 | 5.61 | 5.90 |

EXAMPLE III 2-(1-(Ethoxyimino)propyl)-3-hydroxy-5-(3-(5-(methylsulfonyl)-2-pyridyloxy)phenyl)cyclohex-2-en-1-one

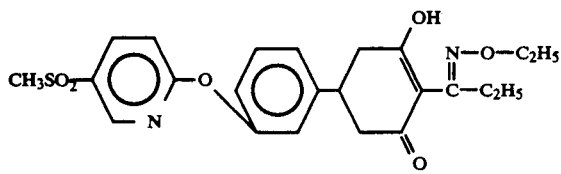

A partially dissolved mixture of 64.5 g (0.155 mol) of 2-propionyl-3-hydroxy-5-(3-(5-(methylsulfonyl)-2-pyridyloxy)phenyl)cyclohex-2-en-1-one in 200 mL of $CH_2Cl_2$ and 700 mL of absolute ethanol was treated with 17.7 g (0.186 mol) of ethoxyamine hydrochloride and 15.3 g (0.186 mol) of sodium acetate. The resulting slurry was stirred for 20 hours at room temperature. The slurry was poured into 3 liters (L) of water and the $CH_2Cl_2$ layer was thoroughly removed. The $CH_2Cl_2$ layer was dried over $MgSO_4$, filtered and the $CH_2Cl_2$ evaporated off to yield a pale oily residue. The residue was passed through a short column of silica gel (about 300 g), eluting with $CH_2Cl_2$. Evaporation of the initial 2 L of eluent afforded a pale oil. This oil was dissolved in 400 mL of diethyl ether which briefly formed a clear solution before precipitating the product as a white solid. The product was filtered and dried in vacuo to afford 63.5 g (89 percent of theoretical) of the above indicated product as a white crystalline solid. The product melted at 125.5°–128° C.; $^1H$ NMR ($CDCl_3$): δ1.17 (t, 3H, —N=CCH$_2$C$\underline{H}_3$), 1.32 (t, 3H, —OCH$_2$C$\underline{H}_3$), 2.68–3.62 (m includes s at 3.10, 10H, —N=CC$\underline{H}_2$—, ring C$\underline{H}_2$CHC$\underline{H}_2$—, C$\underline{H}_3$SO$_2$—), 4.18 (q, 2H, —OC$\underline{H}_2$—), 7.05–7.58 (m, 5H, ArH's), 8.22 (dd, 1H, ArH), 8.78 (d, 1H, ArH), 15.1 (br s, 1H, enol H) (Compound 3).

| Analysis | percent | | |
|---|---|---|---|
| | C | H | N |
| Calc. for $C_{23}H_{26}N_2O_6S$ | 60.20 | 5.72 | 6.11 |
| Found | 60.30 | 5.77 | 6.03 |

EXAMPLE IV 2-(1-(Ethoxyimino)propyl)-3-hydroxy-5-(3-(5-(methylthio)-2-pyridyloxy)phenyl)cyclohex-2-en-1-one

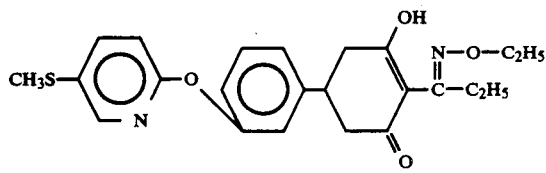

A mixture of 2.1 g (0.0055 mol) of 2-propionyl-3-hydroxy-5-(3-(5-(methylthio)-2-pyridyloxy)phenyl)cyclohex-2-en-1-one, 0.45 g (0.0061 mol) of ethoxyamine hydrochloride and 0.50 g (0.0061 mol) of sodium acetate in 8 mL of dichloromethane and 12 mL of absolute ethanol was stirred under a nitrogen atmosphere at room temperature for about 20 hours. The reaction mixture was poured into 100 mL of water and extracted thrice with 10 mL portions of dichloromethane. The solvent extracts were combined, dried over $MgSO_4$, filtered through silica gel and the solvent removed by evaporation leaving a residue which solidified upon standing. Recrystallization of the residue from hexane gave the above named product in a yield of 2.2 g (94 percent of theoretical). The product melted at 75°–78° C.; $^1H$ NMR ($CDCl_3$): δ1.08–1.52 (m, 6H, both —CH$_2$C$\underline{H}_3$'s), 2.45 (s, 3H, —SCH$_3$), 2.60–3.65 (m, 7H, —CH(CH$_2$)$_2$ and —C$\underline{H}_2$CH$_3$), 6.80–7.55 (m, 5H, ArH's), 7.75 (dd, J=9 Hz and 2H, 1H, ArH), 8.18 (d, J=2 Hz, ArH), 15.1 (br s, 1H, enol H) (Compound 4).

| Analysis | percent | | |
|---|---|---|---|
| | C | H | N |
| Calc. for $C_{23}H_{26}N_2O_4S$ | 64.8 | 6.15 | 6.57 |
| Found | 64.5 | 6.27 | 6.41 |

EXAMPLE V 2-(1-(Ethoxyimino)propyl)-3-hydroxy-5-(4-(5-(methylsulfonyl)-2-pyridylthio)phenyl)cyclohex-2-en-1-one

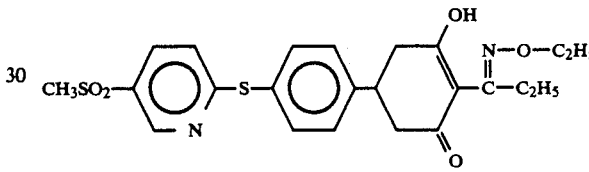

To a slurry of 4.60 g (0.0107 mol) of 2-propionyl-3-hydroxy-5-(4-(5-(methylsulfonyl)-2-pyridylthio)-phenyl)cyclohex-2-en-1-one in 100 mL of methylene chloride and 100 mL of 95 percent ethanol was added 1.35 g (0.0139 mol) of ethoxyamine hydrochloride and 1.31 g (0.0160 mol) of anhydrous sodium acetate. The slurry was stirred at ambient temperature for 12 hours and diluted with 100 mL of methylene chloride and washed thrice with 150 mL portions of water. The organic layer was dried over sodium sulfate and the solvent was removed in vacuo leaving 4.8 g (94.7 percent of theoretical) of the crude product. The product was purified by column chromatography using 5:95 acetone:methylene chloride as eluent and then trituration with diethyl ether affording 2.60 g (51.3 percent of theoretical) of the above named title compound, melting at 125.5°–128.5° C.; $^1H$ NMR ($CDCl_3$): δ 1.05–1.40 (m, 6H, C$\underline{H}_3$CH$_2$— and C$\underline{H}_3$CH$_2$O—), 2.55–3.55 (m, 11H, ring protons, CH$_3$SO$_2$—, CH$_3$C$\underline{H}_2$—), 4.10 (q, 2H, CH$_3$C$\underline{H}_2$O—), 6.9–8.85 (m, 7H, ArH), 15.0 (broad s, br, 1H, OH).

| Analysis: | percent | | |
|---|---|---|---|
| | C | H | N |
| Calc. for $C_{23}H_{26}N_2O_5S_2$: | 58.20 | 5.52 | 5.90 |
| Found: | 57.71 | 5.56 | 5.84 |

EXAMPLE VI 2-(1-(Ethoxyimino)propyl)-3-hydroxy-5-(4-(5-(trifluoromethyl)-3-fluoro-2-pyridylthio)phenyl)cyclohex-2-en-1-one

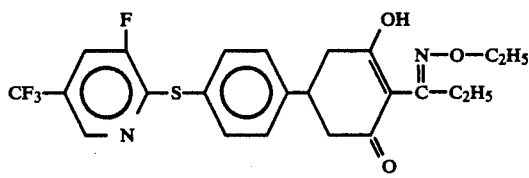

To a slurry of 2.10 g (0.00478 mol) of 2-propionyl-3-hydroxy-5-(4-((5-(trifluoromethyl)-3-fluoro-2-pyridylthio)phenyl)cyclohex-2-en-1-one in 75 mL of ethanol was added 0.61 g (0.0621 mol) of o-ethylhydroxyamine hydrochloride and 0.59 g (0.00717 mol) of anhydrous sodium acetate. The slurry was stirred at ambient temperature for 19 hours and then diluted with 100 mL of methylene chloride and 150 mL of water. The organic layer was separated and washed twice with 150 mL portions of water and dried over sodium sulfate. The solvent was removed in vacuo leaving 2.05 g (89 percent of theoretical) of the crude product. The product was purified by column chromatography using methylene chloride as eluent. Recrystallization form hexane afforded 1.6 g (70 percent of theoretical) of the above named title compound, melting at 91°-92° C.; $R_f$ 0.36 (silica gel, 20:80 acetone:hexane), $^1$H NMR (CDCl$_3$): δ 1.0-1.4 (m, 6H, C$\underline{H}_3$CH$_2$— and C$\underline{H}_3$CH$_2$O—), 2.50-3.65 (m, 7H, ring protons and CH$_3$C$\underline{H}_2$—), 4.05 (q, 2H, CH$_3$C$\underline{H}_2$O—), 7.15-8.65 (m, 6H, Ar$\underline{H}$), 15.0 (broad s, 1H, O$\underline{H}$).

| Analysis | percent | | |
|---|---|---|---|
| | C | H | N |
| Calc. for C$_{23}$H$_{22}$F$_4$N$_2$O$_3$S | 57.25 | 4.60 | 5.81 |
| Found | 57.33 | 4.67 | 5.78 |

EXAMPLE VII

2-Propionyl-3-hydroxy-5-(3-(5-methylthio-b 2-pyridyloxy)phenyl)cyclohex-2-en-1-one

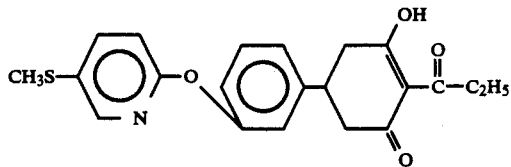

To a solution of 4.5 g (0.040 mol) of potassium t-butoxide in 40 mL of dimethyl sulfoxide was added, in portions, 5.2 g (0.020 mol) of 2-propionyl-3-hydroxy-5-(3-hydroxyphenyl)cyclohex-2-en-1-one at room temperature over a 10 minute period. The mixture was stirred for an additional 30 minutes and 4.7 g (0.023 mol) of 2-bromo-5-methylthiopyridine was added. The resulting mixture was heated to 100° C. and stirred for 5 hours. The reaction mixture was cooled to room temperature and poured into 250 mL of ice cold water and washed with 100 mL of diethyl ether. The mixture was acidified (pH 2) with 1N HCl and the solution was extracted three times with 50 mL portions of dichloromethane. The organic layers were combined, dried over MgSO$_4$, filtered through silica gel and the solvent removed by evaporation leaving a residue which solidified upon standing. Recrystallization of the residue from methanol gave the above named product as a tan solid in a yield of 6.8 g (89 percent of theoretical) which melted at 65°-80° C.; $^1$H NMR (CDCl$_3$): δ 1.10 (t, J=7 Hz, 3H, C$\underline{H}_3$CH$_2$—), 2.42 (s, 3H, —SCH$_3$), 2.65-3.61 (m, 7H, ring CH(CH$_2$)$_2$ and CH$_3$C$\underline{H}_2$—), 6.84-7.80 (m, 6H, aromatics), 8.22 (d, J=2 Hz, 1H, aromatics), 18.0 (s, 1H, enol H).

| Analysis | percent | | |
|---|---|---|---|
| | C | H | N |
| Calc. for C$_{21}$H$_{21}$NO$_4$S | 65.8 | 5.52 | 3.65 |
| Found | 65.7 | 5.65 | 3.41 |

EXAMPLE VIII

2-Propionyl-3-hydroxy-5-(4-(5-methylsulfonyl-2-pyridyloxy)phenyl)cyclohex-2-en-1-one

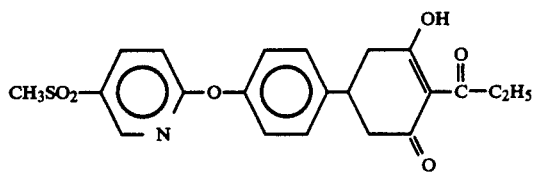

A solution of 3.3 g (0.029 mol) of potassium t-butoxide in 40 mL of dimethyl sulfoxide was treated with 3.5 g (0.013 mol) of 2-propionyl-3-hydroxy-5-(4-hydroxyphenyl)cyclohex-2-en-1-one at room temperature. The mixture was stirred for 10 minutes and 4.1 g (0.017 mol) of 2,5-bis(methylsulfonyl)pyridine was added. The resulting mixture was stirred for 1 hour, becoming dark and homogeneous. The mixture was poured into 200 mL of cold, dilute (0.1N) NaOH and washed with 50 mL of diethyl ether. The aqueous alkaline layer was removed and acidified (pH 2) with 1N HCl and the solution was extracted 4 times with 50 mL portions of ethyl acetate. The organic layers were combined and washed with an aqueous saturated NaCl solution, dried over MgSO$_4$, filtered and the solvent removed by evaporation leaving a solid residue. Recrystallization of the residue from a 1:4 ethyl acetate/absolute ethanol mixture gave the above named product as a beige-white solid in a yield of 4.5 g (80 percent of theoretical). The product melted at 163°-164.5° C.; $^1$H NMR (CDCl$_3$): δ 1.13 (t, 3H, C$\underline{H}_3$—), 2.63-3.75 (m includes at 3.07 for CH$_3$SO$_2$—, 7H ring protons and —C$\underline{H}_2$CH$_3$), 7.03-7.42 (m, 5H, ArH's), 8.25 (dd, 1H, Ar$\underline{H}$), 8.77 (d, 1H, Ar$\underline{H}$), 18.2 (s, 1H, enol $\underline{H}$).

| Analysis | percent | | |
|---|---|---|---|
| | C | H | N |
| Calc. for C$_{21}$H$_{21}$NO$_6$S | 60.70 | 5.10 | 3.37 |
| Found | 59.80 | 5.03 | 3.13 |

EXAMPLE IX

2-Propionyl-3-hydroxy-5-(4-(5-methylsulfonyl-2-pyridylthio)phenyl)cyclohex-2-en-1-one

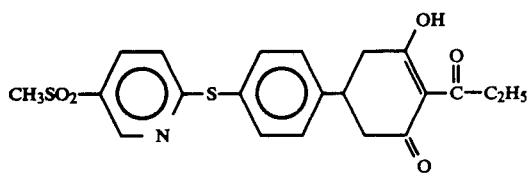

To a solution of 8.0 g (0.029 mol) of 3-hydroxy-5-(4-mercaptophenyl)-2-propionyl-cyclohex-2-en-1-one in 150 mL of acetonitrile was added 6.80 g (0.0290 mol) of 2,5-bis(methylsulfonyl)pyridine and 8.0 g (0.0579 mol) of powdered potassium carbonate. The mixture was heated at reflux for 3 hours and cooled. The mixture was diluted with 500 mL of water and 50 mL of 1.0N NaOH and filtered through Celite®. The filtrate was acidified (pH 2) with concentrated HCl and extracted 4 times with 300 mL of methylene chloride. The organic layer was washed twice with 150 mL portions of water and dried over MgSO$_4$. The solvent was removed in vacuo leaving 10.4 g (83 percent of theoretical) of the crude product which was purified by column chromatography using methylene chloride as the eluent. Recrystallization of the crude from ethanol gave the above named product in a yield of 5.10 g (41 percent of theoretical). The product melted at 167°–174° C.; $^1$H NMR (CF$_3$CO$_2$H): δ 1.25 (t, 3H, C$\underline{H}_3$CH$_2$—), 2.8–3.7 (m, 10H, ring protons and C$\underline{H}_3$SO$_2$—, CH$_3$C$\underline{H}_2$—), 7.3–8.9 (m, 7H, ArH).

EXAMPLE X

2-Propionyl-3-hydroxy-5-(4-(5-(trifluoromethyl)-3-fluoro-2-pyridylthio)phenyl)cyclohex-2-en-1-one

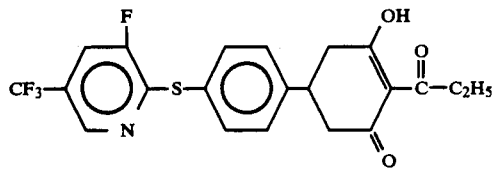

To a solution of 4.0 g (0.0145 mol) of 3-hydroxy-5-(4-mercaptophenyl)-2-propionyl-cyclohex-2-en-1-one in 50 mL of acetonitrile was added 3.90 g (0.0212 mol) of 2,3-difluoro-5-(trifluoromethyl)pyridine and 4.50 g (0.0326 mol) of powdered potassium carbonate. The mixture was stirred one hour at ambient temperature and then heated at reflux for 1.5 hours and cooled to room temperature. The reaction mixture was diluted with 150 mL of water and 150 mL of methylene chloride. The organic layer was separated, washed twice with 150 mL portions of water and dried over Na$_2$SO$_4$. The solvent was removed in vacuo leaving 5.7 g of the crude product which was purified by column chromatography using methylene chloride as the eluent. Recrystallization of the crude from ethanol gave the above named product in a yield of 2.25 g (35 percent of theoretical). The product melted at 152°–154° C.; $^1$H NMR (CDCl$_3$): δ 1.10 (t, 3H, C$\underline{H}_3$CH$_2$—), 2.55–3.65 (m, 7H, ring protons and CH$_3$C$\underline{H}_2$—), 7.15–8.50 (m, 6H, ArH), 18.2 (s, 1H, OH).

| Analysis | percent | | |
|---|---|---|---|
| | C | H | N |
| Calc. for C$_{21}$H$_{17}$F$_4$NO$_3$S | 57.40 | 3.90 | 3.19 |
| Found | 57.70 | 3.94 | 3.07 |

EXAMPLE XI

2-Propionyl-3-hydroxy-5-(4-(5-(trifluoromethyl)-3-fluoro-2-pyridyloxy)phenyl)cyclohex-2-en-1-one

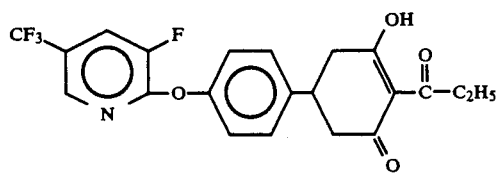

To a slurry of 7.5 g (0.0204 mol) of 3-hydroxy-5-(4-(5-(trifluoromethyl)-3-fluoro-2-pyridyloxy)phenyl)cyclohex-2-en-1-one in 75 mL of benzene was added 2.84 g (0.0218 mol) of propionic anhydride and 5.34 g (0.0437 mol) of 4-dimethylaminopyridine. The slurry was stirred at ambient temperature for 1 hour and heated at reflux for 3 hours. The solution was cooled to room temperature and washed thoroughly with water then with 1N HCl and dried over sodium sulfate. The solvent was removed in vacuo leaving 7.7 g (89.5 percent of theoretical) of the above named compound, as a crude product. The product was further purified by dissolving it in methylene chloride and passing it through a short column of silica gel using methylene chloride as the eluent. The solvent was removed in vacuo leaving 6.2 g (72 percent of theoretical) of the above named compound, as white crystals melting at 154°–156° C.; R$_f$0.29 (silica gel, 20:80 acetone:hexane), $^1$H NMR (CDCl$_3$): δ 1.0 (t, 3H, —CH$_2$CH$_3$), 2.4–3.6 (m, 7H, ring protons and —C$\underline{H}_2$CH$_3$), 7.05–8.25 (m, 6H, ArH), 18.1 (s, 1H, —OH).

| Analysis | percent | | |
|---|---|---|---|
| | C | H | N |
| Calc. for C$_{21}$H$_{17}$F$_4$NO$_4$ | 59.57 | 4.05 | 3.31 |
| Found | 59.66 | 4.13 | 3.20 |

EXAMPLE XII

3-Hydroxy-5-(4-(5-(trifluoromethyl)-3-fluoro-2-pyridyloxy)phenyl)cyclohex-2-en-1-one

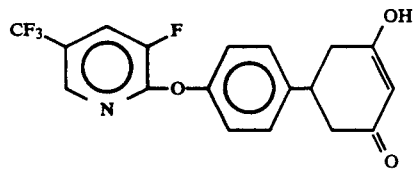

A solution of 33.1 g (0.0753 mol) of 3-hydroxy-5-(4-(5-(trifluoromethyl)-3-fluoro-2-pyridyloxy)-phenyl)-4-(carboethoxy)cyclohex-2-en-1-one in 300 mL (0.30 mol) of 1N sodium hydroxide was heated at 60° C. for 6 hours and cooled to room temperature. The solution was filtered and the filtrate acidified with 30 mL of concentrated HCl and the desired product crystallized out of the solution. The crude product was recovered by filtration and the filtrate thoroughly washed with water and dried in vacuo at 100° C. leaving 23.9 g (86.6 percent of theoretical) of the product which melted at 162°–167° C. The product was further purified by heating it in refluxing methylene chloride, cooling anf filtering. The product was recovered in a yield of 19.6 g (71.0 percent of theoretical) melted at 173°–176° C., with decomposition; $R_f$-0.48 (silica gel, 75:24:1 EtOAc:hexane:HOAc), $^1$H NMR (CDCl$_3$+D$_6$—DMSO): δ 2.35–2.80 (m, 4H, —CH$_2$—), 3.40 (m, 1H, —CH—), 5.41 (s, 1H, vinyl), 7.1–8.37 (m, 6H, ArH), 9.5–11 (b, 1H, —OH).

| Analysis: | percent | | |
|---|---|---|---|
| | C | H | N |
| Calc. for C$_{18}$H$_{13}$F$_4$NO$_3$: | 58.86 | 3.57 | 3.81 |
| Found: | 58.40 | 3.52 | 3.97 |

EXAMPLE XIII

3-Hydroxy-5-(4-(5-(trifluoromethyl)-3-fluoro-2-pyridyloxy)phenyl)-4-(carboethoxy)cyclohex-2-en-1-one

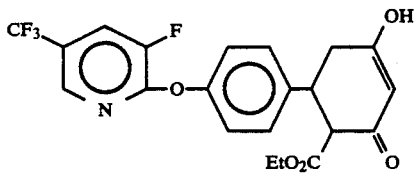

In a 1.0 liter flask was dissolved 2.4 g (0.104 mol) of freshly cut sodium metal in 10 mL of absolute ethanol. To this solution was added a solution of 15.6 g (0.0975 mol) of diethyl malonate in 25 mL of absolute ethanol followed by a solution of 30.2 g (0.0928 mol) of 1-(4-(5-(trifluoromethyl)-3-fluoro-2-pyridyloxy)phenyl)but-1-en-3-one in 75 mL of absolute ethanol. The mixture was stirred at ambient temperature for 6 hours and a cream colored solid precipitated from the solution. The mixture was then diluted with 250 mL of water and the solid slowly dissolved therein. To this solution was slowly added 12 mL of concentrated HCl and the desired product crystallized out of the solution. The product was recovered by filtration, thoroughly washed with water and dried in vacuo. The product melted at 161°–163° C., with decomposition; $R_f$-0.32 (silica gel, 10:90 MeOH:CHCl$_3$), $^1$H NMR (CDCl$_3$): δ 1.0 (t, 3H, CH$_3$CH$_2$—), 2.3–3.1 (m, 2H, ring protons), 3.4–3.75 (m, 2H, ring protons), 3.96 (q, 2H, CH$_3$CH$_2$—), 5.39 (s, 1H, vinyl), 7.10–8.2 (m, 6H, aromatic), 9.0–11.7 (b, 1H, —OH).

| Analysis | percent | | |
|---|---|---|---|
| | C | H | N |
| Calc. for C$_{21}$H$_{17}$F$_4$NO$_5$ | 57.40 | 3.90 | 3.19 |
| Found | 57.39 | 4.05 | 3.16 |

EXAMPLE XIV 1-(4-(5-(Trifluoromethyl)-3-fluoro-2-pyridyloxy)-phenyl)but-1-en-3-one

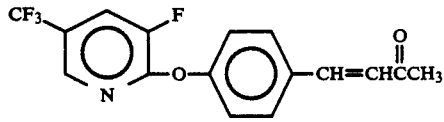

To a slurry of 28.5 g (0.10 mol) of 4-(5-(trifluoromethyl)-3-fluoro-2-pyridyloxy)benzaldehyde in 250 mL of acetone and 250 mL of water was added 7.5 mL of 1N sodium hydroxide. The slurry was stirred at ambient temperature for 19 hours and then diluted with 300 mL of methylene chloride and 200 mL of water and made acidic to a pH of 2 with concentrated HCl. The organic layer was separated in a separatory funnel and washed with 500 mL of water and dried over sodium sulfate. The solvent was removed in vacuo leaving 32.5 g (100 percent of theoretical) of the above named compound, as the crude product. The above named product (melting at 71°–72.5° C.) was recovered in a yield of 27.9 g (85.8 percent of theoretical) after recrystallization of the crude product from hexane; $R_f$-0.19 (silica gel, 15:85 EtOAc:hexane), $^1$H NMR (CDCl$_3$): δ 2.35 (s, 3H, —CH$_3$), 6.65 (d, 1H, J=15 Hz, vinyl), 7.15–8.3 (m, 6H, ArH and vinyl).

| Analysis | percent | | |
|---|---|---|---|
| | C | H | N |
| Calc. for C$_{16}$H$_{11}$F$_4$NO$_2$ | 59.08 | 3.41 | 4.31 |
| Found | 59.30 | 3.44 | 4.27 |

EXAMPLE XV 4-(5-(Trifluoromethyl)-3-fluoro-2-pyridyloxy)benzaldehyde

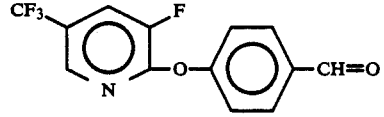

To a solution of 36.6 g (0.20 mol) of 2,3-difluoro-5-(trifluoromethyl)pyridine in 150 ml of acetonitrile was added 25.6 g (0.21 mol) of p-hydroxybenzaldehyde, 29.0 g (0.21 mol) of powdered potassium carbonate and 50 mL of acetonitrile. The slurry was stirred at ambient temperature for 21 hours and then diluted with 300 mL of water. The organic layer was separated in a separatory funnel and washed twice with 150 mL portions of water followed by washing with 100 mL of a 10 percent potassium carbonate solution. The mixture was then dried over sodium sulfate and the solvent removed in vacuo leaving 48.0 g (84 percent of theoretical) of the above named compound, a light yellow oil, as the product; $^1$H NMR (CDCl$_3$): 7.3–8.3 (m, 6H, Ar), 10.0 (s, 1H, CH(O).

EXAMPLE XVI

2-Propionyl-3-hydroxy-5-(4-hydroxyphenyl)cyclohex-2-en-1-one

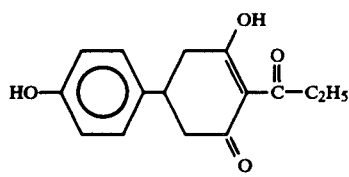

A solution of 21 g (0.060 mol) of 2-propionyl-3-hydroxy-5-(4-benzyloxyphenyl)cyclohex-2-en-1-one in 250 mL of ethyl acetate and 250 mL of absolute ethanol was treated with 12 mL (0.12 mol) of cyclohexene and 0.7 g of 20 percent palladium hydroxide on carbon (Pearlman's catalyst) and the mixture was heated at reflux for 5 hours. The reaction mixture was cooled slightly and filtered through diatomaceous earth. Evaporation of the filtrate from the mixture gave a crude solid residue. Recrystallization of the residue from a 1:1 ethyl acetate-hexane mixture gave the above named product as a beige crystalline solid in a yield of 13.7 g (88 percent of theoretical). The product melted at 135°–137° C. $R_f$ 0.45 (silica gel, 10:90 MeOH:CHCl$_3$), $^1$H NMR (CDCl$_3$): δ 1.13 (t, 3H, —C$\underline{H}_3$), 2.55–3.50 (m, 7H, ring protons and —C$\underline{H}_2$CH$_3$), 6.60–7.12 (m, 5H, ArH's and ArO$\underline{H}$), 18.15 broad s, 1H, enol $\underline{H}$).

| Analysis | percent | |
|---|---|---|
| | C | H |
| Calc. for C$_{15}$H$_{16}$O$_4$ | 69.20 | 6.20 |
| Found | 69.0 | 6.29 |

EXAMPLE XVII

2-Propionyl-3-hydroxy-5-(4-benzyloxyphenyl)cyclohex-2-en-1-one

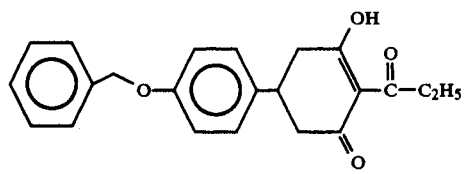

A mixture of 54 g (0.13 mol) of 2-propionyl-3-hydroxy-5-(4-benzyloxyphenyl)-4-(carboethoxy)cyclohex-2-en-1-one and 30 g (0.37 mol) of 50 percent sodium hydroxide in 450 mL of 95 percent ethanol and 100 mL of water was stirred mechanically and heated at about 70° C. for 16 hours. The resulting clear yellow solution was cooled to about 60° C. and treated with 50 mL of concentrated HCl. The product precipitated from the solution and was isolated by filtration. Recrystallization from absolute ethanol gave the above named product as a beige crystalline solid in a yield of 24 g (54 percent of theoretical). The product melted at 114°–115° C.; $^1$H NMR (CDCl$_3$): δ 1.17 (t, 3H, —CH$_3$), 2.60–3.48 (m, 7H, ring protons and —CH$_2$CH$_3$), 5.05 (s, 2H, ArCH$_2$O—), 6.83–7.55 (m, 9H, Ar$\underline{H}$'s), 18.1 (s, 1H, enol, H).

| Analysis | percent | |
|---|---|---|
| | C | H |
| Calc. for C$_{22}$H$_{22}$O$_4$ | 75.4 | 6.33 |
| Found | 75.1 | 6.39 |

EXAMPLE XVIII

2-Propionyl-3-hydroxy-5-(4-benzyloxyphenyl)-4-(carboethoxy)cyclohex-2-en-1-one

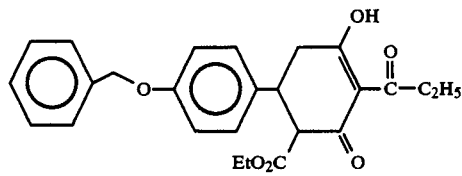

A well stirred slurry of 54 g (0.15 mol) of 3-hydroxy-5-(4-benzyloxyphenyl)-4-(carboethoxy)cyclohex-2-en-1-one in 500 mL of chloroform was treated sequentially with 24 g (0.18 mol) of propionic anhydride, 23 g (0.29 mol) of pyridine and 3.0 g (0.025 mol) of 4-dimethylaminopyridine. The resulting solution was heated at 70° C. for 10 hours. The solution was then cooled to about room temperature and washed twice with 400 mL portions of 1N HCl then with 400 mL of an aqueous saturated sodium chloride solution, dried over MgSO$_4$, filtered and the solvent evaporated off to leave a yellow oil which crystallized on standing. Recrystallization from absolute ethanol gave the above named product as a light yellow crystalline solid in a yield of 57 g (90 percent of theoretical). The product melted at 106°–109° C.; $^1$H NMR (CDCl$_3$): δ 0.92–1.25 (m, 6H, CH$_3$'s), 2.67–3.22 (m including q at 3.08, 4H, —CH$_2$CH$_3$ and ring CH$_2$), 3.55–3.80 (m, 2H, ring —C$\underline{H}$—C$\underline{H}$—), 4.05 (q, 2H, CO$_2$CH$_2$—), 5.02 (s, 2H, ArCH$_2$O—), 6.82–7.50 (m, 9H, ArH's), 8.18 (br, s, 1H, enol H).

| Analysis | percent | |
|---|---|---|
| | C | H |
| Calc. for C$_{25}$H$_{26}$O$_6$ | 71.1 | 6.20 |
| Found | 70.8 | 6.28 |

EXAMPLE XIX

3-Hydroxy-5-(4-benzyloxyphenyl)-4-(carboethoxy)cyclohex-2-en-1-one

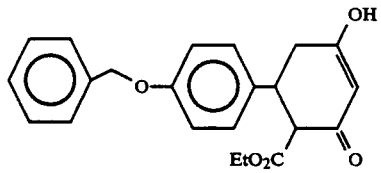

A solution of sodium ethoxide was prepared by dissolving 5.3 g (0.23 mol) of sodium metal in 350 mL of absolute ethanol. This solution was treated dropwise, at room temperature, with a solution of 34 g (0.21 mol) of diethyl malonate in 25 mL of ethanol and stirred at room temperature for 30 minutes. To this solution was added 48 g (0.23 mol) of 1-(4-benzyloxyphenyl)but-1- en-3-one in solid portions and the mixture stirred for 20 hours. The reaction mixture was diluted with 2 L of water, acidified with concentrated HCl and extracted thrice with 400 mL portions of ethyl acetate. The organic layers were combined, dried over MgSO$_4$, filtered and concentrated to a volume of 500 mL. Upon cooling the product precipitated and was recovered by filtration and dried to give the above named product, as a white crystalline solid, in a yield of 57 g (69 percent of theoretical). The product melted at 153°-155° C.; $^1$H NMR (CDCl$_3$—DMSO—d$_6$): δ 1.00 (t, 3H, CH$_3$—), 2.40-2.75 (m, 2H, ring CH$_2$), 3.40-3.65 (m, 2H, ring —CH—CH—), 3.95 (q, 2H, —OCH$_2$CH$_3$), 5.00 (s, 2H, ArCH$_2$), 5.46 (s, 1H, HC=C=), 6.78-7.45 (m, 9H, ArH's).

| Analysis: | percent | |
|---|---|---|
| | C | H |
| Calc. for C$_{22}$H$_{22}$O$_5$: | 72.1 | 6.05 |
| Found: | 71.5 | 6.12 |

EXAMPLE XX 1-(4-Benzyloxyphenyl)but-1-en-3-one

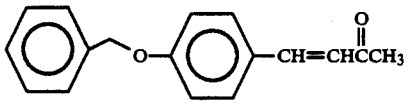

A solution of 50 g (0.2 mol) of 4-benzyloxybenzaldehyde in 500 mL of acetone was diluted with 500 mL of water. To the cloudy emulsion which formed was added 20 mL of 1N sodium hydroxide and the mixture stirred at room temperature for 20 hours. The solids which precipitated were recovered by filtration. Recrystallizaton from methanol gave the above named product, as a tan flasky solid, in a yield of 51 g (87 percent of theoretical). The product melted at 102°-109° C.; $^1$H NMR (CDCl$_3$): δ 2.29 (s, 3H, CH$_3$—), 5.04 (s, 2H, —CH$_2$—), 6.48-7.52 (m, 11H, ArH's and —CH=CH—).

| Analysis: | percent | |
|---|---|---|
| | C | H |
| Calc. for C$_{17}$H$_{16}$O$_2$: | 80.9 | 6.39 |
| Found: | 80.6 | 6.43 |

EXAMPLE XXI

2-Propionyl-3-hydroxy-5-(3-hydroxyphenyl)cyclohex-2-en-1-one

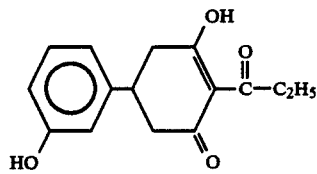

A solution of 36.0 g (0.0926 mol) of 3-hydroxy-5-(3-propionyloxyphenyl)-2-propionyl-4-(carboethoxy)cyclohex-2-en-1-one in 520 mL of 1N NaOH was heated at 75° C. for 4 hours and cooled to room temperature. The reaction mixture was filtered and the filtrate was diluted with 100 mL of water and acidified with 50 mL of concentrated HCl with the product precipitating as an oil. The oil was dissolved in a mixture of 300 mL of methylene chloride and 200 mL of ethyl ether. The organic layer was separated, washed twice with 200 mL portions of water and dried over Na$_2$SO$_4$. The solvent was removed in vacuo leaving 20.4 g of a partially crystalline product which was purified by column chromatography using a 20:80 acetone-chloroform mixture as eluent. The fractions containing the product were combined and the solvent removed in vacuo leaving 13.1 g (54.4 percent of theoretical) of the above named product which melted at 124°-131° C.; R$_f$0.38 (silica gel, 10:90 methanol:chloroform), $^1$H NMR (CDCl$_3$+D$_6$—DMSO): δ 1.10 (t, 3H, —CH$_2$CH$_3$), 2.5-3.5 (m, 7H, ring protons and —CH$_2$CH$_3$), 6.55-7.25 (m, 3H, ArH), 8.85 (s, H, ArOH), 18.1 (s, 1H, OH).

| Analysis: | percent | |
|---|---|---|
| | C | H |
| Calc. for C$_{15}$H$_{16}$O$_4$: | 69.21 | 6.20 |
| Found: | 68.84 | 6.17 |

EXAMPLE XXII

3-Hydroxy-5-(3-propionyloxyphenyl)-2-propionyl-4-(carboethoxy)cyclohex-2-en-1-one

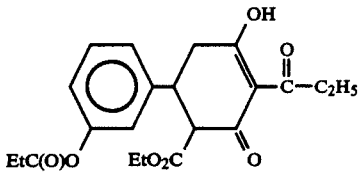

To a solution of 26.5 g (0.959 mol) of 3-hydroxy-5-(3-hydroxyphenyl)-4-(carboethoxy)cyclohex-2-en-1-one in 200 mL of benzene was added 27.5 g (0.211 mol) of propionic anhydride, 16.7 g (0.211 mol) of pyridine and 2.93 g (0.024 mol) of 4-dimethylaminopyridine. The solution was stirred at ambient temperature for 1 hour and at reflux for 4 hours and cooled to room temperature. The reaction mixture was diluted with 150 mL of diethyl ether and washed with 250 mL of 1N HCl and then with 150 mL of water and dried over Na$_2$SO$_4$. The solvent was removed in vacuo leaving 36.1 g (97 percent of theoretical) of the above named product as a light orange colored oil; R$_f$0.49 (silica gel, 50:50 ethyl acetate and 1 percent acetic acid), $^1$H NMR (CDCl$_3$): δ 0.9-1.4 (m, 9H, —CH$_2$CH$_3$), 2.1-4.3 (m, 10H, ring protons and —CH$_2$CH$_3$), 6.9-7.45 (m, 4H, ArH), 18.2 (b, 1H, OH).

EXAMPLE XXIII 3-hydroxy-5-(3-hydroxyphenyl)-4-(carboethoxy)cyclohex-2-en-1-one

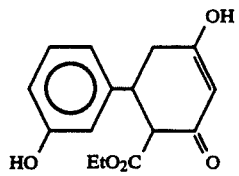

To a solution of 4.72 g (0.205 mol) of freshly cut sodium metal dissolved in absolute ethanol was added 16.8 g (0.105 mol) of diethyl malonate in 25 mL of absolute ethanol. To this solution was added 16.2 g (0.10 mol) of 1-(3-hydroxyphenyl)but-1-en-3-one, prepared as described by Marrion et al. in *J. Biochem.* vol. 45, 533, (1949), and 100 mL of absolute ethanol. The solution was stirred at ambient temperature for 17 hours, diluted with 500 mL of water and acidified with 19 mL of concentrated HCl. The mixture was diluted with 400 mL of methylene chloride and the organic layer separated, washed with 150 mL of water and dried over $Na_2SO_4$. The solvent was removed in vacuo leaving 26.5 g (96 percent of theoretical) of the above named product as a light yellow oil; $^1H$ NMR ($CDCl_3+D_6$—DMSO) δ 0.8–1.3 (m, 3H, —$CH_2C\underline{H}_3$), 2.3–4.3 (m, 6H, ring protons and —$C\underline{H}_2CH_3$), 5.5 (s, 1H, —CH=), 6.5–7.2 (m, 4H, ArH), 6.8 (b, 1H, ArOH), 18.0 (b, 1H, OH).

EXAMPLE XXIV

2-Propionyl-3-hydroxy-5-(4-mercaptophenyl)cyclohex-2-en-1-one

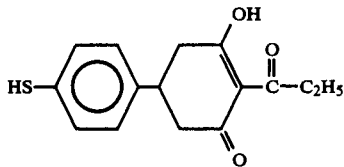

To 5 g (0.0163 mol) of 2-propionyl-3-hydroxy-5-(4-(methylsulfinyl)phenyl)cyclohex-2-en-1-one in a flask cooled in an ice-water bath was added 25 mL (0.177 mol) of trifluoroacetic anhydride dropwise over 5 minutes. The ice-water bath was removed and the solution stirred at ambient temperature for 3 hours. The solvent was removed in vacuo and the oil remaining was dissolved in 82 mL of 1N NaOH and the solution stirred at ambient temperature overnight. The mixture was diluted with 1200 mL of water, filtered and the filtrate acidified with 5 mL of concentrated HCl with the product precipitating as an oily solid. The product was dissolved in 150 mL of methylene chloride and the solution washed twice with 150 mL portions of water and dried over $Na_2SO_4$. Removal of the solvent in vacuo gave the above named product in a yield of 4.0 g (88.7 percent of theoretical).

EXAMPLE XXV

2-Propionyl-3-hydroxy-5-(4-(methylsulfinyl)-phenyl)-cyclohex-2-en-1-one

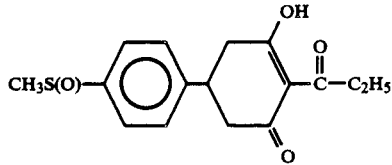

To a solution of 51.6 g (0.178 mol) of 2-propionyl-3-hydroxy-5-(4-(methylthio)phenyl)cyclohex-2-en-1-one (prepared as in U.S. Pat. No. 4,555,263) in 150 mL of methylene chloride and 150 mL of glacial acetic acid was added 20.15 g (0.178 mol) of 30 percent hydrogen peroxide dropwise over twenty minutes. The reaction temperature rose from 20° to 28° C. at which point, the reaction mixture was placed in a cold water bath. After 20 minutes, an additional 6.75 g (0.0595 mol) of 30 percent hydrogen peroxide was added dropwise and the mixture was stirred at ambient temperature for 3 hours. The mixture was diluted with 150 mL of methylene chloride, washed thrice with 250 mL portions of water and then with 200 mL of aqueous sodium bicarbonate. The organic layer was separated and dried over $Na_2SO_4$ and the solvent removed in vacuo leaving 51.6 g (94.8 percent of theoretical) of the above named product melting at 111°–117° C. Recrystallization of the residue from 2-propanol gave the pure product in a yield of 46.1 g (84.7 percent of theoretical). The product melted at 116°–117° C.; $R_f$-0.07 (silica gel, 50:50 ethyl acetate-hexane and 1.0 percent acetic acid), $^1H$ NMR ($CDCl_3$): δ 1.1 (t, 3H, —$CH_2C\underline{H}_3$), 2.70 (s, 3H, $CH_3SO$—), 2.7–3.7 (m, 7H, ring protons and —$C\underline{H}_2CH_3$), 7.25–7.70 (m, 4H, ArH), 18.1 (s, 1H, OH).

| Analysis: | percent | |
|---|---|---|
| | C | H |
| Calc. for $C_{16}H_{18}O_4S$: | 62.72 | 5.92 |
| Found: | 63.02 | 5.94 |

EXAMPLE XXVI 3-hydroxy-5-(3-hydroxyphenyl)cyclohex-2-en-1-one

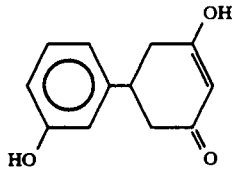

A solution of 20 g (0.068 mol) of 3-hydroxy-5-(3-benzyloxyphenyl)cyclohex-2-en-1-one in 250 mL of absolute ethanol was treated with 7.5 g of 5.0 percent palladium on carbon and shaken in a Parr ® hydrogenator under 50 pounds of hydrogen pressure for 2 hours at room temperature. The reaction mixture was filtered through diatomaceous earth, diluted with 1 L of water and extracted thrice with 100 mL portions of ethyl acetate. The combined extracts were washed with an aqueous saturated NaCl solution, dried over $MgSO_4$, filtered, concentrated and cooled to precipitate the desired above named product as a greyish-white solid in a yield of 9.8 g (71 percent of theoretical). The product melted at 140°–150° C./dec.

| Analysis: | percent | |
|---|---|---|
| | C | H |
| Calc. for $C_{12}H_{12}O_3$: | 70.6 | 5.92 |
| Found: | 69.0 | 6.18 |

By following the hereinabove procedures of Examples I, II, III and IV employing the appropriate starting cyclohex-2-en-1-one and amine reactants, the following compounds in Table V are prepared.

TABLE V

| Compd. No. | COMPOUND | M.P. °C. | Mol. Formula | Elem. Analysis C | H | N |
|---|---|---|---|---|---|---|
| 5 | [structure: 3-F, 5-CF₃ pyridyl-O-phenyl-cyclohexenone with OH, N—O—Et, C—Pr] | 81-81.5 | C₂₄H₂₄F₄N₂O₄ | Calc'd 59.99 Found 60.01 | 5.04 5.02 | 5.83 5.82 |
| 6 | [structure: 5-CF₃ pyridyl-O-phenyl-cyclohexenone with OH, N—O—Et, C—Et] | 83-84 | C₂₃H₂₃F₃N₂O₄ | Calc'd 61.60 Found 61.8 | 5.17 5.18 | 6.25 6.14 |
| 7 | [structure: 3-F, 5-CF₃ pyridyl-O-dimethylphenyl-cyclohexenone with OH, N—O—Et, C—Et] | 108-111 | C₂₅H₂₆F₄N₂O₄ | Calc'd 60.72 Found 60.75 | 5.30 5.34 | 5.67 5.54 |
| 8 | [structure: 3-Cl, 5-CF₃ pyridyl-O-phenyl-cyclohexenone with OH, N—O—Et, C—Et] | 89-89.5 | C₂₃H₂₂ClF₃N₂O₄ | Calc'd 57.20 Found 57.21 | 4.59 4.55 | 5.80 5.74 |
| 9 | [structure: 3-Cl, 5-CF₃ pyridyl-O-phenyl-cyclohexenone with OH, N—O—CH₂CH=Et, C—Et] | 75.5-76.5 | C₂₄H₂₂ClF₃N₂O₄ | Calc'd 58.24 Found 58.25 | 4.48 4.38 | 5.66 5.55 |
| 10 | [structure: 3-F, 5-CF₃ pyridyl-CH₂O-phenyl-cyclohexenone with OH, N—O—Et, C—Et] | Oil | C₂₃H₂₂F₄N₂O₄ | Calc'd 59.22 Found 59.23 | 4.75 4.56 | 6.01 5.90 |
| 11 | [structure: 3-F, 5-CF₃ pyridyl-CH₂O-phenyl-cyclohexenone with OH, N—O—Et, C—Pr] | Oil | C₂₄H₂₄F₄N₂O₄ | Calc'd 59.99 Found 60.00 | 5.04 4.95 | 5.83 5.78 |
| 12 | [structure: 3-Cl, 5-CF₃ pyridyl-CH₂O-phenyl-cyclohexenone with OH, N—O—Et, C—Me] | 86-89 | C₂₂H₂₀ClF₃N₂O₄ | Calc'd 56.35 Found 56.39 | 4.30 4.28 | 5.98 5.88 |
| 13 | [structure: 3-Cl, 5-CF₃ pyridyl-CH₂O-phenyl-cyclohexenone with OH, N—O—Et, C—Et] | 74-75 | C₂₃H₂₂ClF₃N₂O₄ | Calc'd 57.20 Found 57.20 | 4.59 4.61 | 5.80 5.78 |

TABLE V-continued

| Compd. No. | COMPOUND | M.P. °C. | Mol. Formula | Elem. Analysis C | H | N |
|---|---|---|---|---|---|---|
| 14 | (3,5-dichloropyridin-2-yloxy)methyl-phenyl cyclohexanedione with N-O-Et, C-Pr oxime | Oil | $C_{23}H_{24}Cl_2N_2O_4$ | Calc'd 59.62 Found 58.73 | 5.22 5.20 | 6.05 5.93 |
| 15 | (3,5-dichloropyridin-2-yloxy)methyl-phenyl cyclohexanedione with N-O-Et, C-Et oxime | 72.5-75.5 | $C_{22}H_{22}Cl_2N_2O_4$ | Calc'd 58.80 Found 58.73 | 4.94 4.97 | 6.24 6.14 |
| 16 | (5-methylsulfonylpyridin-2-yloxy)methyl-phenyl cyclohexanedione with EtO$_2$C, N-O-Et, C-Et | 55-65 | $C_{26}H_{30}N_2O_8S$ | Calc'd 58.90 Found 58.24 | 5.70 5.79 | 5.28 5.27 |
| 17 | (3,5-dichloropyridin-2-yloxy)-phenyl cyclohexanedione with N-O-Et, C-Et oxime | 107-108 | $C_{22}H_{22}Cl_2N_2O_4$ | Calc'd 58.80 Found 59.40 | 4.94 4.96 | 6.23 6.29 |
| 18 | (3,5-dichloropyridin-2-yloxy)-phenyl cyclohexanedione with EtO$_2$C, N-O-Et, C-Et | 112.5-116 | $C_{25}H_{26}Cl_2N_2O_6$ | Calc'd 57.60 Found 57.80 | 5.00 5.20 | 5.37 5.20 |
| 19 | (5-trifluoromethylpyridin-2-yloxy)methyl-phenyl cyclohexanedione with N-O-Et, C-Et oxime | 71-72 | $C_{23}H_{23}F_3N_2O_4$ | Calc'd 61.60 Found 61.50 | 5.17 5.10 | 6.25 6.24 |
| 20 | (3,5-dichloropyridin-2-yloxy)methyl-phenyl cyclohexanedione with N-O-Et, C-Et oxime | Oil | $C_{22}H_{22}Cl_2N_2O_4$ | Calc'd 58.80 Found 58.36 | 4.94 4.90 | 6.23 6.10 |
| 21 | (3-fluoro-5-trifluoromethylpyridin-2-yloxy)methyl-(bromo)phenyl cyclohexanedione with N-O-Et, C-Et oxime | Oil | $C_{23}H_{21}BrF_4N_2O_4$ | Calc'd 50.65 Found 50.74 | 3.88 3.90 | 5.14 5.10 |

TABLE V-continued

| Compd. No. | COMPOUND | M.P. °C. | Mol. Formula | Elem. Analysis | C | H | N |
|---|---|---|---|---|---|---|---|
| 22 | [structure: 4-CF3, 3-F, 6-OCH3 pyridyl-O-phenyl-cyclohexenone with N-O-Et, C-Et, OH, =O] | 87-88 | $C_{24}H_{24}F_4N_2O_5$ | Calc'd<br>Found | 58.06<br>58.14 | 4.87<br>4.84 | 5.64<br>5.61 |
| 23 | [structure: 5-CF3-pyridyl-O-phenyl-cyclohexenone with N-O-Et, C-Et, OH, =O] | Oil | $C_{23}H_{23}F_3N_2O_4$ | Calc'd<br>Found | 61.60<br>61.60 | 5.17<br>5.04 | 6.25<br>6.24 |
| 24 | [structure: 4-CF3, 3-F pyridyl-O-(F-phenyl)-cyclohexenone with N-O-Et, C-Et, OH, =O] | Oil | $C_{23}H_{21}F_5N_2O_4$ | Calc'd<br>Found | 57.02<br>56.36 | 4.37<br>4.22 | 5.78<br>5.72 |
| 25 | [structure: 2-CH3S-pyrimidinyl-O-phenyl-cyclohexenone with N-O-Et, C-Et, OH, =O] | Oil | $C_{22}H_{25}N_3O_4S$ | Calc'd<br>Found | 61.80<br>61.60 | 5.89<br>5.90 | 9.82<br>9.75 |
| 26 | [structure: 5-Br-pyrimidinyl-O-phenyl-cyclohexenone with N-O-Et, C-Et, OH, =O] | Oil | $C_{21}H_{22}BrN_3O_4$ | Calc'd<br>Found | 54.80<br>54.50 | 4.82<br>4.82 | 9.20<br>9.13 |
| 27 | [structure: 5-CH3SO2-pyridyl-S-phenyl-cyclohexenone with N-O-Et, C-Et, OH, =O] | 125-128.5 | $C_{23}H_{26}N_2O_5S_2$ | Calc'd<br>Found | 58.20<br>57.71 | 5.52<br>5.56 | 5.90<br>5.84 |
| 28 | [structure: pyridyl-O-phenyl-cyclohexenone with N-O-Et, C-Et, OH, =O] | 57-62 | $C_{21}H_{23}N_3O_4$ | Calc'd<br>Found | 66.10<br>66.00 | 6.08<br>5.93 | 11.00<br>11.10 |
| 29 | [structure: 4-CF3, 6-Cl-pyridyl-O-phenyl-cyclohexenone with N-O-Et, C-Et, OH, =O] | 83-84 | $C_{23}H_{22}ClF_3N_2O_4$ | Calc'd<br>Found | 57.20<br>57.10 | 4.59<br>4.52 | 5.80<br>5.61 |

TABLE V-continued

| Compd. No. | COMPOUND | M.P. °C. | Mol. Formula | Elem. Analysis C H N | | |
|---|---|---|---|---|---|---|
| 30 | [2-(3-CF₃-6-Cl-pyridin-2-yloxy)phenyl cyclohexanedione oxime ether structure] | 95–96.5 | $C_{23}H_{22}ClF_3N_2O_4$ | Calc'd 57.20 4.59 5.80 Found 57.10 4.51 5.68 | | |
| 31 | [3-CH₃S-pyridin-2-yloxy phenyl structure] | Oil | $C_{23}H_{26}N_2O_4S$ | Calc'd 64.8 6.15 6.57 Found 65.30 6.24 6.61 | | |
| 32 | [3-CF₃-pyridin-2-yloxy phenyl structure] | 60–61 | $C_{23}H_{23}F_3N_2O_4$ | Calc'd 61.60 5.17 6.25 Found 61.50 5.11 6.17 | | |
| 33 | [4,6-dimethylpyrimidin-2-yloxy phenyl structure] | Oil | $C_{23}H_{27}N_3O_4$ | Calc'd 67.50 6.65 10.30 Found 67.50 6.64 10.40 | | |
| 34 | [5-CN-pyridin-2-yloxy phenyl structure] | Oil | $C_{23}H_{23}N_3O_4$ | Calc'd 68.10 5.72 10.40 Found 68.00 5.78 10.40 | | |
| 35 | [3-CH₃SO₂-pyridin-2-yloxy phenyl structure] | Oil | $C_{23}H_{26}N_2O_6S$ | Calc'd 60.2 5.72 6.11 Found 60.26 5.92 6.25 | | |
| 36 | [5-CH₃-pyrimidin-2-yloxy phenyl structure] | Oil | $C_{22}H_{25}N_3O_4$ | Calc'd 66.80 6.37 10.60 Found 67.10 6.38 10.20 | | |
| 37 | [4-CH₃SO₂-pyridin-2-yloxy phenyl structure with N—O—CH₂CH:CHCl] | 45–65 | $C_{24}H_{25}ClN_2O_6S$ | Calc'd 57.10 4.99 5.55 Found 57.10 4.86 5.53 | | |

TABLE V-continued

| Compd. No. | COMPOUND | M.P. °C. | Mol. Formula | Elem. Analysis | C | H | N |
|---|---|---|---|---|---|---|---|
| 38 | CH₃SO₂-pyridyl-O-C₆H₄-cyclohexenone with OH, N-O-CH₂CH:CH₂, Et | Oil | $C_{24}H_{26}N_2O_6S$ | Calc'd<br>Found | 61.30<br>61.20 | 5.57<br>5.47 | 5.95<br>5.94 |
| 39 | CH₃SO₂-pyrimidinyl-O-C₆H₄-cyclohexenone with OH, N-O-Et, Et | 136–138.5 | $C_{22}H_{25}N_3O_6S$ | Calc'd<br>Found | 57.50<br>57.20 | 5.48<br>5.42 | 9.14<br>9.04 |
| 40 | 2,6-bis(CF₃)-pyridyl-O-C₆H₄-cyclohexenone with OH, N-O-Et, Et | 146.5–148 | $C_{24}H_{22}F_6N_2O_4$ | Calc'd<br>Found | 55.80<br>55.50 | 4.29<br>4.30 | 5.42<br>5.40 |
| 41 | 5-CH₃-4-CH₃SO₂-pyrimidinyl-O-C₆H₄-cyclohexenone with OH, N-O-Et, Et | Oil | $C_{23}H_{27}N_3O_6S$ | Calc'd<br>Found | 58.30<br>58.20 | 5.75<br>5.75 | 8.87<br>8.63 |
| 42 | 5-CH₃-4-CH₃S-pyrimidinyl-O-C₆H₄-cyclohexenone with OH, N-O-Et, Et | Oil | $C_{23}H_{27}N_3O_4S$ | Calc'd<br>Found | 62.60<br>63.00 | 6.16<br>6.15 | 9.52<br>9.58 |
| 43 | 4,6-bis(CH₃S)-1,3,5-triazinyl-O-C₆H₄-cyclohexenone with OH, N-O-Et, Et | Oil | $C_{22}H_{26}N_4O_4S_2$ | Calc'd<br>Found | 55.7<br>55.6 | 5.52<br>5.54 | 11.8<br>11.8 |
| 44 | 5-F-4-CH₃S-pyrimidinyl-O-C₆H₄-cyclohexenone with OH, N-O-Et, Et | Oil | $C_{22}H_{24}FN_3O_4S$ | Calc'd<br>Found | 59.30<br>59.37 | 5.43<br>5.38 | 9.43<br>9.35 |
| 45 | CH₃SO₂-pyridyl-O-C₆H₄-cyclohexenone with OH, N-O-Et, Et | 103–105 | $C_{24}H_{28}N_2O_6S$ | Calc'd<br>Found | 61.0<br>61.3 | 5.97<br>5.95 | 5.93<br>5.81 |

TABLE V-continued

| Compd. No. | COMPOUND | M.P. °C. | Mol. Formula | Elem. Analysis C H N |
|---|---|---|---|---|
| 46 | (structure: 3,5-dichloro-4-methylsulfonylphenoxy linked to phenyl-cyclohexenone oxime ether with EtO₂C substituent) | | $C_{26}H_{28}Cl_2N_2O_8S$ | Calc'd<br>Found |
| 47 | (structure: 5-methylsulfonyl-pyridin-2-yloxy linked to phenyl-cyclohexenone oxime ether with CH₃ substituent) | | $C_{24}H_{28}N_2O_6S$ | Calc'd<br>Found |
| 48 | (structure: methylsulfonyl-pyrimidinyloxy linked to phenyl-cyclohexenone oxime ether) | Oil | $C_{22}H_{25}N_3O_6S$ | Calc'd 57.5 5.48 9.14<br>Found 57.7 5.50 9.94 |
| 49 | (structure: 5-trifluoromethyl-pyrimidin-2-yloxy linked to phenyl-cyclohexenone oxime ether) | | $C_{22}H_{22}F_3O_4$ | Calc'd<br>Found |
| 50 | (structure: 3-methylthio-pyridazin-6-yloxy linked to phenyl-cyclohexenone oxime ether) | Oil | $C_{22}H_{25}N_3O_6S$ | Calc'd 59.6 5.68 9.47<br>Found 58.5 5.65 9.32 |
| 51 | (structure: 4,6-dimethoxy-pyrimidin-2-yloxy linked to phenyl-cyclohexenone oxime ether) | Oil | $C_{23}H_{27}N_3O_6$ | Calc'd 62.6 6.17 9.52<br>Found 62.8 6.23 9.46 |
| 52 | (structure: 6-isopropylthio-pyridin-2-yloxy linked to phenyl-cyclohexenone oxime ether) | Oil | $C_{25}H_{30}N_2O_4S$ | Calc'd 66.05 6.65 6.16<br>Found 66.39 6.78 6.20 |
| 53 | (structure: 4-isopropylthio-pyridin-2-yloxy linked to phenyl-cyclohexenone oxime ether) | 59.5–60.5 | $C_{25}H_{30}N_2O_4S$ | Calc'd 66.05 6.65 6.16<br>Found 66.34 6.78 6.17 |

TABLE V-continued

| Compd. No. | COMPOUND | M.P. °C. | Mol. Formula | Elem. Analysis C | H | N |
|---|---|---|---|---|---|---|
| 54 | i-C$_3$H$_7$SO$_2$-pyridine-O-phenyl-cyclohexenyl(OH)(C(Et)=N-O-Et) | 62–68 | C$_{25}$H$_{30}$N$_2$O$_6$S | Calc'd 61.7 Found 61.9 | 6.21 6.02 | 5.76 5.76 |
| 55 | i-C$_3$H$_7$SO$_2$-pyridine-O-phenyl-cyclohexenyl(OH)(C(Et)=N-O-Et) | 75–78.5 | C$_{25}$H$_{30}$N$_2$O$_6$S | Calc'd 61.7 Found 62.1 | 6.21 6.20 | 5.76 5.79 |
| 56 | CH$_3$S-pyridine-O-phenyl-cyclohexenyl(OH)(C(Et)=N-O-Et) | Oil | C$_{23}$H$_{26}$N$_2$O$_4$S | Calc'd 64.8 Found 65.3 | 6.15 6.18 | 6.57 6.58 |
| 57 | CH$_3$-pyridine-O-phenyl-cyclohexenyl(OH)(C(Et)=N-O-Et) | 96–97.5 | C$_{23}$H$_{26}$N$_2$O$_4$ | Calc'd 70.0 Found 70.2 | 6.64 6.65 | 7.10 7.02 |
| 58 | CH$_3$S-(F)pyridine-O-(F)phenyl-cyclohexenyl(OH)(C(Et)=N-O-Et) | | C$_{23}$H$_{24}$F$_2$N$_2$O$_4$S | Calc'd Found | | |
| 59 | CF$_3$-(F)pyridine-S-phenyl-cyclohexenyl(OH)(C(Et)=N-O-Et) | 91–92 | C$_{23}$H$_{22}$F$_4$N$_2$O$_3$S | Calc'd 57.25 Found 57.33 | 4.60 4.67 | 5.81 5.78 |
| 60 | CF$_3$-pyridine-O-phenyl-cyclohexenyl(EtO$_2$C)(OH)(C(Et)=N-O-Et) | Oil | C$_{26}$H$_{27}$F$_3$N$_2$O$_6$ | Calc'd 60.0 Found 60.1 | 5.23 5.20 | 5.38 5.38 |
| 61 | EtSO$_2$-pyridine-O-phenyl-cyclohexenyl(OH)(C(Et)=N-O-Et) | Oil | C$_{24}$H$_{28}$N$_2$O$_6$S | Calc'd 61.0 Found 61.0 | 5.97 6.01 | 5.93 5.93 |
| 62 | EtS-pyridine-O-phenyl-cyclohexenyl(OH)(C(Et)=N-O-Et) | Oil | C$_{24}$H$_{28}$N$_2$O$_4$S | Calc'd 65.4 Found 65.6 | 6.41 6.57 | 6.36 6.15 |

TABLE V-continued

| Compd. No. | COMPOUND | M.P. °C. | Mol. Formula | Elem. Analysis C | H | N |
|---|---|---|---|---|---|---|
| 63 | CH3S(O)- pyridine-O-CH2-phenyl-cyclohexenyl with OH, N-O-Et, C-Et | 84–87 | $C_{23}H_{26}N_2O_5S$ | Calc'd 62.4 Found 62.94 | 5.92 5.99 | 6.33 6.06 |
| 64 | Br- pyridine-O-CH2-phenyl-cyclohexenyl with OH, N-O-Et, C-Et | 100.5–102 | $C_{22}H_{23}BrN_2O_4$ | Cald'd 57.5 Found 57.7 | 5.05 5.09 | 6.10 5.94 |
| 65 | CH3SO2- pyridine-O-CH2-phenyl-cyclohexenyl with OH, N-O-Et, C-Et | 84–88 | $C_{23}H_{26}N_2O_6S$ | Calc'd 60.2 Found 60.1 | 5.72 5.64 | 6.11 6.16 |
| 66 | EtS- pyridine-O-CH2-phenyl-cyclohexenyl with OH, N-O-Et, C-Et | Oil | $C_{24}H_{28}N_2O_4S$ | Calc'd 65.43 Found 65.42 | 6.41 6.42 | 6.36 6.43 |
| 67 | EtSO2- pyridine-O-CH2-phenyl-cyclohexenyl with OH, N-O-Et, C-Et | 88.5–91 | $C_{24}H_{28}N_2O_6S$ | Calc'd 61.0 Found 61.0 | 5.97 6.07 | 5.93 5.71 |
| 68 | CF3- pyridine-O-CH2-phenyl-cyclohexenyl with OH, N-O-Et, C-Et | Oil | $C_{23}H_{23}F_3N_2O_4$ | Calc'd 61.6 Found 61.5 | 5.17 5.08 | 6.25 6.17 |

The compounds of the present invention have been found to be suitable for use in methods for the pre- and postemergent control of many annual and perennial grassy weeds. In addition, the present compounds are sufficiently tolerated by most broadleaf crops, such as, for example, soybeans, cotton and sugarbeet to allow for the postemergent control of grassy weeds growing among said crops.

It is to be noted that while all compounds have herbicidal activity, each compound/active ingredient may have a slightly different degree of herbicidal activity on different plants. Some compounds may be more active in the control of one specific weed species than another and some compounds may be more selective toward one crop species than another. Many of these compounds are unique because of their systemic action and because of the very low levels of chemical required to control the grassy weeds.

For such uses, unmodified active ingredients of the present invention can be employed. However, the compounds may be prepared in formulations/compositions as dusts, wettable powders, flowable concentrates, or emulsifiable concentrates by the admixture of the active compounds with inert materials, known in the art as inert agricultural adjuvants and/or carriers, in solid or liquid form.

Thus, for example, the active compound(s) can be admixed with one or more additives including organic solvents, petroleum distillates, water or other liquid carriers, surface active dispersing agents, and finely divided inert solids. For example, an active ingredient can be dispersed on a finely-divided solid and employed herein as a dust or granule. Also, the active ingredients, as liquid concentrates or solid compositions comprising one or more of the active ingredients, can be dispersed in water, typically with aid of a wetting agent, and the resulting aqueous dispersion employed as a spray. In other procedures, the active ingredients can be employed in a constituent of organic liquid compositions, oil-in-water and water-in-oil emulsions or water dispersions, with or without the addition of wetting, dispersing, or emulsifying agents.

The herbicidally effective concentration of the active ingredients in solid or liquid compositions generally is from about 0.0003 to about 95 percent by weight or more. Concentrations from about 0.05 to about 50 percent by weight are often employed.

The compound can be employed in the form of diluted flowable compositions or a wettable powder composition containing 2 to 10,000 ppm of one or more of the compounds, preferably 10 to 600 ppm are employed. When the carrier contains a surface active agent, from about 0.1 to about 20 percent by weight of the active ingredient is advantageously employed. Depending upon the concentration in the composition, such augmented compositions are adapted to be employed for the control of the undesirable plants or employed as concentrates and subsequently diluted with additional inert carrier, e.g. water, to produce the ultimate treating compositions.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water. In such compositions, the active ingredient is usually present in a concentration from about 5 to about 98 weight percent.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. With dusts, good results can usually be obtained employing compositions containing from about 0.1 to about 2.0 percent or more by weight of toxicant.

Granular formulations are usually prepared by impregnating a solution of the toxicant in a volatile organic solvent onto a bed of coarsely divided attapulgite, bentonite, diatomite, or the like.

Emulsifiers which can be advantageously employed herein can be readily determined by those skilled in the art and include various nonionic, anionic and cationic emulsifiers, or a blend of two or more of said emulsifiers.

Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with the polyol or polyoxyalkylene.

Anionic emulsifiers include the oil-soluble salts (e.g., calcium) of alkylaryl sulphonic acids, oil soluble salts of sulphated polyglycol ethers and appropriate salts of phosphated polyglycol ether. Cationic emulsifiers include quaternary ammonium compounds and fatty amines.

The preferred emulsifiers will depend upon the nature of the emulsifiable concentrate. For example, an emulsifiable concentrate of a compound of Formula I containing 200 g/L of the compound in xylene may require a blend of an ethoxylated nonyl phenol and calcium dodecyl benzene sulphonate to function effectively whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions; mineral oils substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol. Mixtures of two or more organic liquids are also often suitably employed in the preparation of the emulsifiable concentrate. The preferred organic liquids are xylene, and propyl benzene fractions, with xylene being most preferred.

The surface active dispersing agents are usually employed in liquid compositions and in the amount of from 0.1 to 20 percent by weight of the combined weight of the dispersing agent and active compound.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines and blends of surfactant with mineral or vegetable oils.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oat, Johnson grass and the like, while showing high selectivity to important broadleaf crops such as cotton, sunflower, sugarbeet, rape and soybeans. These compounds are also uniquely effective in selectively controlling perennial grassy weeds such as Johnson grass and the like in the presence of said crop plants.

The exact amount of the active material to be applied is dependent not only on the specific active ingredient being applied, but also on the particular action desired, the plant species to be controlled and the stage of growth thereof as well as the part of the plant to be contacted with the toxic active ingredient. Thus, all of the active ingredients of the present invention and compositions containing the same may not be equally effective at similar concentrations or be equally effective against the same plant species.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

In postemergent operations a dosage of about 0.01 to about 20 lbs/acre (0.056–22.4 kg/hectare) is generally applicable, although not all compounds are equally effective and some weeds are more difficult to control. Thus, a dosage rate in the range of about 0.05 to about 1.0 lb/acre (0.01–1.12 kg/hectare) is preferred in postemergent control of annual grassy weeds, while about 0.05 to about 5 lbs/acre (0.056–5.6 kg/hectare) is a preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

Representative formulations/compositions of the present invention include the following:

Emulsifiable Concentrate

TABLE VI

| Ingredient | weight percent of total composition |
| --- | --- |
| Compound No. 3 | 6.4 |
| Atlox TM 3454$^a$ | 5.4 |
| Atlox TM 3413$^a$ | 5.4 |
| Aromatic 100 | 41.4 |
| Cyclohexanone | 41.4 |

TABLE VII

| Ingredient | weight percent of total composition |
| --- | --- |
| Compound No. 4 | 5.0 |
| Xylene | 65.0 |
| Hallcomid TM M8-10$^b$ | 20.0 |
| Tenseofix TM B7438$^c$ | 3.0 |
| Tenseofix TM B7453$^c$ | 3.0 |
| Ethomeen TM C25$^d$ | 4.0 |

Wettable Powder

TABLE VIII

| Ingredient | weight percent of total composition |
| --- | --- |
| Compound No. 3 | 25.0 |
| Barden AG clay | 50.0 |
| Celite TM 209$^e$ | 17.0 |
| Nekal TM BA-75$^f$ | 3.0 |
| Daxad TM 21$^g$ | 5.0 |

TABLE IX

| Ingredient | weight percent of total composition |
| --- | --- |
| Compound No. 4 | 50.0 |
| Barden AG clay | 21.0 |
| Celite TM 209$^e$ | 21.0 |
| Polyfon TM H$^h$ | 5.0 |

TABLE IX-continued

| Ingredient | weight percent of total composition |
| --- | --- |
| Aerosol TM OTB$^i$ | 3.0 |

Flowable Concentrate

TABLE X

| Ingredient | weight percent of total composition |
| --- | --- |
| Compound No. 3 | 12.0 |
| Pluronic TM P105$^j$ | 2.0 |
| Darvan TM #1$^k$ | 0.5 |
| Dow Corning FG10$^m$ | 1.0 |
| VeeGum TM $^n$ | 0.3 |
| Kelzan TM $^o$ | 0.04 |
| Propylene glycol | 4.5 |
| water | 79.66 |

TABLE XI

| Ingredient | weight percent of total composition |
| --- | --- |
| Compound No. 4 | 12.0 |
| Sun Spray TM 11N oil$^p$ | 72.7 |
| Bentone TM 38$^q$ | 1.0 |
| solution of 95% methanol/5% water | 0.3 |
| Emulsogen TM M$^r$ | 12.0 |
| Agrimul TM 70A$^s$ | 2.0 |

Dusts

TABLE XII

| Ingredient | weight percent of total composition |
| --- | --- |
| Compound No. 3 | 5.0 |
| Barden clay | 80.0 |
| Celite TM 209$^e$ | 15.0 |

TABLE XIII

| Ingredient | weight percent of total composition |
| --- | --- |
| Compound No. 4 | 2.5 |
| Barden clay | 82.5 |
| Celite TM 209$^e$ | 15.0 |

In the above Tables:

Aromatic 100=an aromatic hydrocarbon solvent with a Flash point above 101° F. TCC, a product of Exxon Corp.

a=an anionic/nonionic emulsifier product of Atlas Chemical Industries, Inc.

b=N,N'-dimethyl amides of fatty acid, a product of The C. P. Hall Co.

c=blends of calcium dodecylbenzenesulfonates with nonylphenol propylene oxide/ethylene oxide block copolymers, a product of Tenseia, Inc.

d=is a proprietary material of Akzo Chemicals, Inc.

e=diatomaceous earth, a product of Johns-Manville Products, Inc.

f=sodium alkylnaphthalene sulfonate, an anionic emulsifier product of GAF Corp.

g=a polyaryl and substituted benzoid alkylsulfonic acid, a product of W. R. Grace & Co.

h=sugar-free, sodium based sulfonates of Kraft lignin is a proprietary material of West Virginia Pulp and Paper Co.

i=dioctyl ester of sodium sulfosuccinic acid, a product of American Cyanamid Co.

j=condensate of ethylene oxide with hydrophobic bases formed by condensing propylene oxide with propylene glycol, a product of BASF Corp.

k=sodium salts of polymerized alkylnaphthalene sulfonic acid, an anionic surfactant of R. T. Vanderbilt Co., Inc.

m=is a proprietary material of Dow Corning Corp.

n=colliodal magnesium aluminum silicate, a product of R. T. Vanderbilt Co., Inc.

o=a polysaccharide known as xanthan gum, a product of Kelco Co.

p=a phytobland mineral oil also known as spray oil, a product of Sun Oil Co.

q=organic derivative of hydrous magnesium aluminum silicate minerals, a product of National Lead Co.

r=a nonionic ethoxylated derivative-a mineral oil emulsifier of American Hoechst Corp.

s=alkyl aryl polyether alcohol, a product of Henkel Corp.

The following examples illustrate the herbicidal effects of the compounds of this invention.

The plant species employed in these evaluations were as follows:

| Common Name | Scientific Name |
| --- | --- |
| Barnyard grass | Echinochloa crusgalli |
| Yellow Foxtail | Setaria lutescens |
| Johnson grass | Sorghum halepense |
| Wild Oat | Avena fatua |
| Cotton | Gossypium hirsutum |

-continued

| Common Name | Scientific Name |
| --- | --- |
| Oilseed rape | Brassica napus |
| Soybean | Glycine max |
| Sugarbeet | Beta vulgaris |
| Sunflower | Helianthus |

EXAMPLE XXVIII

Pre-Emergent Evaluation

In representative operations, each compound to be utilized in a series of tests is dissolved in acetone to one-half of the final volume (twice the final concentration) to be used and the acetone solution in each case is admixed with an equal volume of water containing 0.1 percent by weight of a non-ionic surfactant TWEEN ® 20 (a polyoxyethylene sorbitan monolaurate). The compositions, generally in the nature of an emulsion, were employed to spray seed beds of separate respective plant species which had been planted in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other seed beds were treated with a acetone/TWEEN ® 20/water mixture containing no test compound to serve as controls. After treatment, the seed beds were maintained for about two weeks under greenhouse conditions conducive for good plant growth and watered as necessary. The specific plant species, test compound and dosage and the percent postemergent control obtained are set forth in Table XIV. Control refers to the reduction in growth compared to the observed results of the same untreated species. Note the "NT" means "not tested."

TABLE XIV

| Compound Tested | Dosage in lb/A | Percent kill and control of Plant Species | | | | | | | | |
| --- | --- | --- | --- | --- | --- | --- | --- | --- | --- | --- |
| | | Cotton | Rape | Soybean | Sugarbeet | Sunflower | Yellow Foxtail | Johnson Grass | Barnyard Grass | Wild Oat |
| 1 | .50 | 0 | 0 | 0 | 0 | 0 | 75 | 0 | 50 | 0 |
|  | 1.0 | 0 | 0 | 0 | 0 | 0 | 95 | NT | 95 | 50 |
| 2 | .25 | 0 | 0 | 0 | 0 | 0 | 80 | 90 | 40 | 35 |
|  | .5 | 0 | 0 | 0 | 0 | 0 | 100 | 100 | 100 | 100 |
|  | 1.0 | 0 | 0 | 0 | 0 | 0 | 100 | 100 | 100 | 100 |
| 3 | .25 | 0 | 0 | 0 | 0 | 0 | 100 | 100 | 100 | 100 |
|  | .5 | 0 | 0 | 0 | 0 | 0 | 100 | 100 | 100 | 100 |
|  | 1.0 | 0 | 0 | 0 | 0 | 0 | 100 | 100 | 100 | 100 |
| 4 | .25 | 0 | 0 | 0 | 0 | 0 | 99 | 100 | 100 | 99 |
|  | .5 | 0 | 0 | 0 | 0 | 0 | 100 | 100 | 100 | 100 |
| 5 | .25 | 0 | 0 | 0 | 0 | 0 | 80 | 0 | 100 | 0 |
|  | .5 | 0 | 0 | 0 | 0 | 0 | 100 | NT | 100 | 0 |
| 6 | 1.0 | 100 | 0 | 35 | 0 | 0 | 100 | 100 | 100 | 100 |
|  | 2.0 | 0 | 0 | 65 | 0 | 0 | 100 | 100 | 100 | 100 |
|  | 4.0 | 0 | 0 | 40 | 35 | 0 | 100 | 100 | 100 | 100 |
| 7 | .25 | 0 | 0 | 0 | 0 | 0 | 90 | 95 | 90 | 25 |
|  | .5 | 0 | 0 | 0 | 0 | 0 | 97 | 90 | 100 | 97 |
| 10 | 1.0 | 0 | 0 | 0 | 0 | 0 | 80 | 100 | 70 | 90 |
|  | 2.0 | 0 | 0 | 0 | 0 | 0 | 100 | 100 | 90 | 100 |
|  | 4.0 | 0 | 0 | 0 | 0 | 0 | 100 | 100 | 100 | 100 |
| 11 | 2.0 | 0 | 0 | 0 | 0 | 0 | 90 | 85 | 30 | 75 |
|  | 4.0 | 0 | 0 | 0 | 0 | 0 | 95 | 100 | 80 | 100 |
| 12 | 1.0 | 0 | 0 | 0 | 0 | 0 | 40 | 0 | 100 | 0 |
| 13 | 1.0 | 0 | 0 | 0 | 0 | 0 | 70 | 100 | 100 | 70 |
| 14 | .5 | 0 | 0 | 0 | 0 | 0 | 95 | 85 | 95 | 0 |
|  | 1.0 | 0 | 0 | 0 | 10 | 0 | 99 | 90 | 90 | 5 |
| 15 | .5 | 0 | 25 | 0 | 0 | 0 | 90 | 90 | 100 | 75 |
|  | 1.0 | 0 | 10 | 0 | 0 | 5 | 99 | 99 | 85 | 80 |
| 17 | 1.0 | 0 | 0 | 0 | 0 | 0 | 100 | 90 | 99 | 95 |
|  | 2.0 | 0 | 0 | 0 | 0 | 0 | 100 | 100 | 100 | 100 |
|  | 4.0 | 0 | 0 | 0 | 0 | 0 | 100 | 100 | 100 | 100 |

TABLE XIV-continued

| Compound Tested | Dosage in lb/A | Percent kill and control of Plant Species | | | | | | | |
|---|---|---|---|---|---|---|---|---|---|
| | | Cotton | Rape | Soybean | Sugarbeet | Sunflower | Yellow Foxtail | Johnson Grass | Barnyard Grass | Wild Oat |
| 18 | 2.0 | 20 | 65 | 0 | 0 | 15 | 0 | 85 | 90 | 90 |
| | 4.0 | 50 | 75 | 55 | 35 | 100 | 0 | 25 | 100 | 95 |
| 19 | 2 | 0 | 0 | 0 | 0 | | 100 | 100 | 100 | 100 |
| 20 | .25 | 0 | 0 | 0 | 0 | 0 | 65 | 93 | 85 | 0 |
| | .5 | 0 | 0 | 0 | 0 | 0 | 80 | 97 | 97 | 25 |
| 21 | 2.0 | 25 | 25 | 0 | 100 | 15 | 100 | 100 | 100 | 100 |
| | 4.0 | 60 | 35 | 0 | 100 | 25 | 100 | 100 | 100 | 95 |
| 22 | 2.0 | 0 | 0 | 0 | 0 | 0 | 100 | 100 | 100 | 99 |
| | 4.0 | 0 | 0 | 0 | 40 | 0 | 100 | 100 | 100 | 100 |
| 23 | 2.0 | 0 | 50 | 0 | 0 | 0 | 100 | 100 | 100 | 88 |
| | 4.0 | 0 | 65 | 0 | 15 | 45 | 100 | 100 | 100 | 100 |
| 26 | .5 | 0 | 0 | 0 | 0 | 0 | 100 | 100 | 100 | 99 |
| 27 | .5 | 0 | 0 | 0 | 0 | 0 | 100 | 100 | 100 | 100 |
| 28 | .25 | 0 | 0 | 0 | 0 | 0 | 100 | 100 | 100 | 97 |
| | .5 | 0 | 0 | 0 | 0 | 0 | 100 | 100 | 100 | 80 |
| 29 | .5 | 0 | 0 | 0 | 0 | 0 | 85 | 95 | 90 | 100 |
| | 1.0 | 0 | 0 | 0 | 0 | 0 | 100 | 95 | 100 | 100 |
| | 2.0 | 0 | 0 | 0 | 0 | 0 | 100 | 50 | 100 | 100 |
| 30 | 1.0 | 0 | 0 | 0 | 0 | 0 | 0 | 0 | 30 | 0 |
| | 2.0 | 0 | 0 | 0 | 40 | 0 | 40 | 70 | 40 | 50 |
| 31 | .25 | 0 | 0 | 0 | 0 | 0 | 99 | 99 | 99 | 97 |
| | .5 | 0 | 0 | 0 | 0 | 0 | 97 | 100 | 99 | 99 |
| 32 | .25 | 0 | 0 | 0 | 0 | 0 | 100 | 100 | 100 | 10 |
| | .5 | 0 | 0 | 0 | 0 | 0 | 100 | 100 | 100 | 20 |
| 33 | 1.0 | 0 | 0 | 0 | 0 | 0 | 90 | 100 | 100 | 90 |
| | 2.0 | 0 | 0 | 0 | 0 | 0 | 99 | 100 | 100 | 99 |
| 35 | .25 | 0 | 0 | 0 | 0 | 0 | 85 | 99 | 97 | 80 |
| | .5 | 0 | 0 | 0 | 0 | 0 | 99 | 99 | 100 | 97 |
| 36 | .5 | 0 | 0 | 0 | 0 | 0 | 100 | 100 | 100 | 100 |
| 37 | .5 | 0 | 0 | 0 | 0 | 0 | 100 | 25 | 60 | 80 |
| | 1.0 | 0 | 0 | 0 | 0 | 100 | 90 | 80 | 100 | 100 |
| 38 | .5 | 0 | 0 | 0 | 0 | 0 | 95 | 20 | 100 | 100 |
| | 1.0 | 0 | 0 | 0 | 0 | 0 | 95 | 100 | 100 | 100 |
| 39 | 1.0 | 0 | 0 | 0 | 0 | 0 | 97 | 30 | 97 | 100 |
| | 2.0 | 0 | 0 | 0 | 0 | 0 | 100 | 85 | 100 | 99 |
| 40 | .25 | 0 | 0 | 0 | 0 | 0 | 99 | 99 | 100 | 60 |
| | .5 | 0 | 0 | 0 | 0 | 0 | 100 | 100 | 100 | 100 |
| 45 | .125 | 0 | 0 | 0 | 0 | 0 | 100 | 65 | 100 | 50 |
| | .25 | 0 | 0 | 0 | 0 | 0 | 100 | 100 | 100 | 100 |
| 51 | .5 | 0 | 0 | 0 | 0 | 0 | 100 | 75 | 95 | 35 |
| 53 | .5 | 0 | 0 | 0 | 0 | 0 | 85 | 70 | 85 | 0 |
| 56 | .25 | 0 | 0 | 0 | 0 | 0 | 100 | 100 | NT | 85 |
| | .5 | 0 | 0 | 0 | 0 | 0 | 100 | 100 | NT | 95 |
| 57 | .25 | 0 | 0 | 0 | 0 | 0 | 75 | 50 | 75 | 50 |
| | .5 | 0 | 0 | 0 | 0 | 0 | 90 | 50 | 85 | 75 |
| 59 | .25 | 0 | 0 | 0 | 0 | 0 | 100 | 85 | 75 | 40 |
| | .5 | 0 | 0 | 0 | 0 | 0 | 100 | 100 | 100 | 75 |
| 60 | 2.0 | 0 | 0 | 0 | 0 | 0 | 0 | 0 | 70 | 85 |
| | 4. | 0 | 55 | 0 | 0 | 0 | 0 | 0 | 75 | 50 |
| 61 | .5 | 0 | 0 | 30 | 0 | 0 | 85 | 80 | 45 | 75 |
| 62 | .25 | 0 | 0 | 0 | 0 | 0 | 40 | 95 | 75 | 95 |
| | .5 | 0 | 0 | 0 | 0 | 0 | 95 | 95 | 75 | 95 |
| 63 | .5 | 0 | 0 | 0 | 0 | 0 | 100 | 95 | NT | 100 |
| | 1.0 | 0 | 0 | 0 | 0 | 0 | 100 | 100 | NT | 100 |
| 64 | .25 | 0 | 0 | 0 | 0 | 0 | 90 | 100 | 100 | 50 |
| | .5 | 0 | 0 | 0 | 0 | 0 | 75 | 100 | 100 | 75 |
| 66 | .25 | 0 | 0 | 0 | 0 | 0 | 95 | 95 | 95 | 45 |
| | .5 | 0 | 0 | 0 | 0 | 0 | 95 | 95 | 95 | 75 |
| 67 | .25 | 0 | 0 | 0 | 0 | 0 | 100 | 95 | 100 | 30 |
| | .5 | 0 | 0 | 0 | 0 | 0 | 100 | 95 | 100 | 95 |
| 68 | 1.0 | 0 | 0 | 0 | 0 | 0 | 100 | 98 | 100 | 80 |
| | 2.0 | 0 | 20 | 0 | 0 | 50 | 100 | 98 | 100 | 95 |
| | 4.0 | 0 | 75 | 0 | 20 | 60 | 100 | 100 | 100 | 99 |

EXAMPLE XXVIX

Postemergent Evaluation

In representative operations, each compound to be utilized in a series of tests is dissolved in acetone to one-half of the final volume (twice the final concentration) to be used and the acetone solution in each case is admixed with an equal volume of water containing 0.1 percent by weight of a non-ionic surfactant TWEEN ® 20 (a polyoxyethylene sorbitan monolaurate). The compositions, generally in the nature of an emulsion, were employed to spray separate respective plant species which had been grown, in a greenhouse, to a height of 2-6 inches in soil of good nutrient content. Sufficient amounts were employed to provide various application rates as listed in the table. The various beds were positioned side by side and exposed to substantially identical conditions of temperature and light. Each bed was maintained so as to prevent any interaction with test compounds in different plant beds. Other plant beds were treated with a acetone/TWEEN ® 20/water mixture containing no test compound to serve as controls. After treatment, the plants were maintained for about 2 weeks under greenhouse conditions conducive for good plant growth and watered as necessary. The specific plant species, test compound and dosage and the percent postemergent control obtained are set forth in Table XV. Control refers to the reduction in growth compared to the observed results of the same untreated species. Note the "NT" means "not tested."

TABLE XV

| Compound Tested | Dosage in PPM | Percent Kill and Control of Plant Species | | | | | | | |
|---|---|---|---|---|---|---|---|---|---|
| | | Cotton | Rape | Soybean | Sugarbeet | Yellow Foxtail | Johnson Grass | Barnyard Grass | Wild Oat |
| 1 | 250 | 0 | 0 | 0 | 30 | 100 | 100 | 80 | 80 |
| | 500 | 0 | 0 | 0 | NT | 100 | 100 | 98 | 98 |
| 2 | 500 | 0 | 0 | 0 | 0 | 100 | 100 | 100 | 100 |
| | 1000 | 0 | 0 | 0 | 0 | 100 | 100 | 100 | 100 |
| 3 | 125 | 0 | 0 | 0 | 0 | 100 | 100 | 100 | 100 |
| | 250 | 0 | 0 | 0 | 0 | 100 | 100 | 100 | 100 |
| 4 | 125 | 0 | 0 | 0 | 0 | 100 | 100 | 100 | 100 |
| | 250 | 0 | 0 | 0 | 0 | 100 | 100 | 100 | 100 |
| 5 | 125 | 0 | 0 | 0 | 0 | 95 | 60 | 20 | 0 |
| | 250 | 15 | 0 | 10 | 50 | 100 | 75 | 50 | 35 |
| | 500 | 15 | 0 | 10 | 20 | 100 | 80 | 80 | 75 |
| | 1000 | 50 | 0 | 25 | 40 | 100 | 98 | 98 | 100 |
| 6 | 250 | 0 | 0 | 0 | 0 | 85 | 100 | 100 | 100 |
| | 500 | 0 | 0 | 0 | 0 | 100 | 100 | 100 | 100 |
| 7 | 62 | 0 | 0 | 0 | 0 | 40 | NT | 40 | 80 |
| | 125 | 0 | 50 | 5 | 0 | 75 | NT | 98 | 75 |
| 8 | 1000 | 0 | 0 | 5 | 0 | 100 | 100 | 90 | 100 |
| 9 | 1000 | 30 | 0 | 30 | 0 | 90 | 80 | 95 | 0 |
| 10 | 500 | 0 | 70 | 0 | 80 | 80 | 100 | 90 | 100 |
| | 1000 | 0 | 70 | 0 | 80 | 100 | 100 | 80 | 100 |
| 11 | 500 | 0 | 0 | 0 | 0 | 60 | 90 | 80 | 100 |
| | 1000 | 0 | 0 | 0 | 0 | 70 | 80 | 70 | 100 |
| 12 | 500 | 0 | 0 | 0 | 0 | 80 | NT | 75 | 60 |
| 13 | 250 | 0 | 0 | 0 | 0 | 85 | NT | 75 | 80 |
| | 500 | 20 | 0 | 20 | 0 | 95 | NT | 75 | 90 |
| 14 | 500 | 0 | 0 | 0 | 0 | 65 | 60 | 75 | 85 |
| 15 | 250 | 0 | 0 | 0 | 0 | 75 | 90 | 80 | 80 |
| | 500 | 0 | 0 | 0 | 0 | 100 | 95 | 90 | 85 |
| 16 | 1000 | 0 | 0 | 0 | 0 | 95 | NT | 90 | 90 |
| 18 | 500 | 0 | 0 | 0 | 0 | 50 | 50 | 50 | 0 |
| 21 | 125 | 60 | 0 | 60 | 50 | 70 | 70 | 0 | NT |
| 22 | 500 | 0 | 0 | 0 | 0 | 100 | 100 | 100 | 100 |
| | 1000 | 0 | 0 | 0 | 0 | 100 | 100 | 100 | 100 |
| 23 | 500 | 0 | 0 | 0 | 0 | 80 | 85 | 100 | 100 |
| | 1000 | 0 | 0 | 0 | 0 | 100 | 100 | 100 | 100 |
| 24 | 500 | 0 | 0 | 0 | 0 | 95 | 100 | 95 | 100 |
| | 1000 | 0 | 0 | 0 | 0 | 85 | 100 | 95 | 100 |
| 26 | 125 | 0 | 0 | 0 | 0 | 90 | 100 | 100 | 50 |
| | 250 | 0 | 0 | 0 | 0 | 100 | 100 | 100 | 100 |
| 27 | 500 | 0 | 0 | 20 | 0 | 90 | 70 | 100 | 100 |
| 28 | 250 | 0 | 0 | 0 | 0 | 90 | 100 | 100 | 100 |
| | 500 | 0 | 0 | 0 | 0 | 100 | 100 | 100 | 100 |
| 29 | 500 | 30 | 0 | 30 | 0 | 60 | 70 | 75 | 80 |
| 30 | 250 | 0 | 0 | 0 | 0 | 0 | 0 | 60 | 0 |
| 32 | 1000 | 0 | 0 | 0 | 0 | 50 | 50 | 75 | NT |
| 33 | 250 | 0 | 0 | 0 | 0 | 80 | 95 | 90 | 85 |
| | 500 | 0 | 0 | 0 | 0 | 100 | 100 | 90 | 90 |
| 36 | 62 | 0 | 0 | 0 | 0 | 100 | 100 | 100 | 100 |
| | 125 | 0 | 0 | 0 | 0 | 100 | 100 | 100 | 100 |
| 37 | 125 | 0 | 0 | 0 | 0 | 85 | 95 | 100 | 100 |
| | 250 | 0 | 0 | 0 | 0 | 100 | 100 | 100 | 100 |
| 38 | 62 | 0 | 0 | 0 | 0 | 100 | 100 | 100 | 100 |
| | 125 | 0 | 0 | 0 | 0 | 100 | 100 | 100 | 100 |
| 39 | 250 | 50 | 0 | 40 | 20 | 70 | 60 | 65 | NT |
| 40 | 500 | 0 | 0 | 0 | 0 | 90 | 80 | 80 | 90 |
| 41 | 1000 | 0 | 0 | 0 | 0 | 25 | 30 | 25 | 25 |
| 42 | 1000 | 0 | 0 | 0 | 0 | 75 | 80 | 45 | 70 |
| 45 | 125 | 0 | 0 | 0 | 0 | 100 | 100 | 100 | 100 |
| | 250 | 0 | 0 | 0 | 0 | 100 | 100 | 100 | 100 |
| 51 | 250 | 0 | 0 | 0 | 0 | 85 | 80 | 85 | 70 |
| 52 | 250 | 0 | 0 | 0 | 0 | 80 | 90 | 75 | 80 |
| 53 | 500 | 0 | 0 | 50 | 0 | 90 | 100 | 90 | 90 |
| 54 | 500 | 0 | 0 | 40 | 0 | 75 | 70 | 75 | 65 |
| 55 | 500 | 0 | 0 | 40 | 0 | 20 | 75 | 40 | 50 |
| 56 | 250 | 0 | 0 | 0 | 50 | 100 | 100 | 100 | 100 |
| 57 | 500 | 0 | 0 | 35 | 30 | 85 | 100 | 100 | 100 |
| 61 | 250 | 0 | 0 | 0 | 0 | 100 | 85 | 88 | 90 |
| 62 | 62 | 0 | 0 | 0 | 0 | 85 | 85 | 80 | 85 |
| | 125 | 0 | 35 | 0 | 0 | 90 | 90 | 90 | 90 |
| 63 | 125 | 0 | 0 | 0 | 0 | 100 | 100 | 100 | 90 |
| 64 | 125 | 0 | 0 | 0 | 40 | 75 | 100 | 90 | 80 |
| 66 | 250 | 0 | 0 | 0 | 0 | 100 | 100 | 100 | 100 |
| | 500 | 0 | 0 | 0 | 0 | 100 | 100 | 100 | 100 |
| 67 | 250 | 0 | 0 | 0 | 0 | 100 | 90 | 100 | 100 |

TABLE XV-continued

| | | Percent Kill and Control of Plant Species | | | | | | | |
|---|---|---|---|---|---|---|---|---|---|
| Compound Tested | Dosage in PPM | Cotton | Rape | Soybean | Sugarbeet | Yellow Foxtail | Johnson Grass | Barnyard Grass | Wild Oat |
| 68 | 500 | 0 | 0 | 0 | 0 | 100 | 100 | 100 | 90 |
| | 1000 | 0 | 0 | 0 | 0 | 100 | 100 | 100 | 90 |

Other compounds, not specifically exemplified, but within the scope of the present invention may also be employed in the same manner as set forth hereinabove to control certain plant species with results commensurate to the above described results.

Various modifications may be made in the present invention without departing from the spirit or scope thereof and it is understood that we limit ourselves only as defined in the appended claims.

What is claimed is:

1. A substituted cyclohexanedione compound corresponding to the formulae

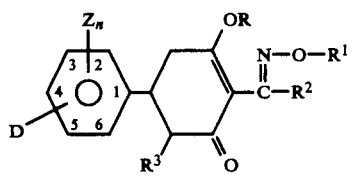

Wherein

D is a group corresponding to one of the formulae,

R represents hydrogen, $C_1$–$C_4$ alkyl, $C_1$–$C_4$ haloalkyl, $C_2$–$C_4$ alkenyl, $C_3$–$C_4$ alkynyl, $C_1$–$C_4$ alkylsulfonyl, phenylsulfonyl or acyl;

$R^1$ represents $C_1$–$C_4$ alkyl, $C_1$–$C_4$ haloalkyl, $C_2$–$C_4$ alkenyl, $C_2$–$C_4$ haloalkenyl, $C_3$–$C_4$ alkynyl, or $C_3$–$C_4$ haloalkynyl;

$R^2$ represents $C_1$–$C_4$ alkyl, $C_1$–$C_4$ fluoroalkyl, $C_1$–$C_4$ alkylthiomethyl, $C_1$–$C_4$ alkoxymethyl, $C_2$–$C_4$ alkenyl or $C_3$–$C_4$ alkynyl;

$R^3$ represents hydrogen or $C_1$–$C_4$ alkoxycarbonyl;

each Z independently represents hydrogen, halo, $C_1$–$C_4$ alkyl, $C_1$–$C_4$ alkoxy or —$CF_3$;

M represents =O, =S, =S(O) or =S(O)$_2$;

Y represents hydrogen, halo, $C_1$–$C_4$ alkyl, $C_1$–$C_4$ alkoxy, $C_1$–$C_4$ alkylthio, $C_1$–$C_4$ alkylsulfinyl or $C_1$–$C_4$ alkylsulfonyl or —$CF_3$, with the proviso that when M is =S(O), Y cannot be $C_1$–$C_4$ alkylthio and when M is =S(O)$_2$, Y cannot be $C_1$–$C_4$ alkylthio or $C_1$–$C_4$ alkylsulfinyl; and n represents the integer 0, 1, 2 or 3;

and the herbicidally acceptable organic and inorganic salts thereof.

2. A compound as defined in claim 1 wherein D

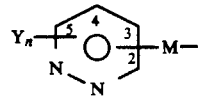

3. A compound as defined in claim 2 wherein R is hydrogen.

4. The compound as defined in claim 3 which is 2-(1-ethoxyimino)propyl)-3-hydroxy-5-(3-(5-methylthio-2-pyridyloxy)phenyl)cyclohex-2-en-1-one.

5. The compound as defined in claim 3 which is 2-(1-ethoxyimino)propyl)-3-hydroxy-5-(3-(5-methyl-sulfonyl-2-pyridyloxy)phenyl)cyclohex-2-en-1-one.

6. A compound as defined in claim 1 wherein D is

7. A compound as defined in claim 1 wherein D is

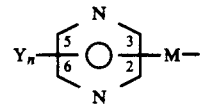

8. A compound as defined in claim 1 wherein D is

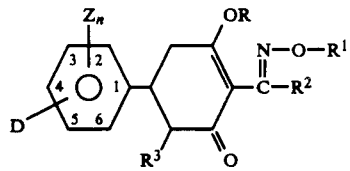

9. A herbicidal composition which comprises an inert carrier in intimate admixture with a herbicidally effective amount of an active ingredient which is a substituted cyclohexanedione compound corresponding to the formula

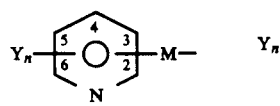

Wherein

D is a group corresponding to one of the formulae,

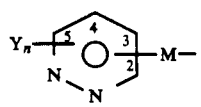

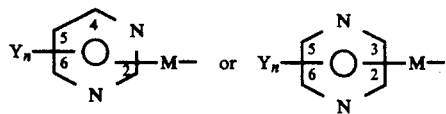

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen or $C_1$-$C_4$ alkoxycarbonyl;

each Z independently represents hydrogen, halo, $C_1$-$C_4$ alkyl, $C_1$-$C_4$ alkoxy or —$CF_3$;

M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl; and n represents the integer 0, 1, 2 or 3;

and the herbicidally acceptable organic and inorganic salts thereof.

10. A composition as defined in claim 9 wherein D is

11. A composition as defined in claim 9 wherein R is hydrogen.

12. The composition as defined in claim 11 wherein the active ingredient is 2-((1-ethoxyimino)propyl)-3-hydroxy-5-(3-(5-methylthio-2-pyridyloxy)phenyl)cyclohex-2-en-1-one.

13. The composition as defined in claim 11 wherein the active ingredient is 2-((1-ethoxyimino)propyl)-3-hydroxy-5-(3-(5-methyl-sulfonyl-2-pyridyloxy)phenyl)-cyclohex-2-en-1-one.

14. A composition as defined in claim 9 wherein D is

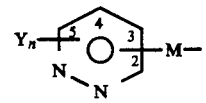

15. A composition as defined in claim 9 wherein D is

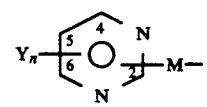

16. A composition as defined in claim 9 wherein D is

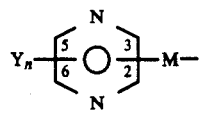

17. A method for the kill or control of grassy weeds which comprises contacting said weeds or their habitat with a herbicidally effective amount of a composition which comprises an inert carrier in intimate admixture with a herbicidally active ingredient which is a substituted cyclohexanedione compound corresponding to the formula

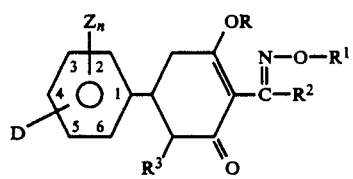

Wherein

D is a group corresponding to one of the formulae,

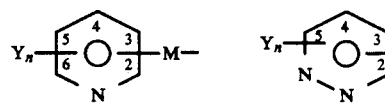

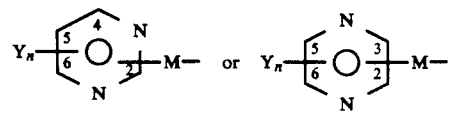

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen or $C_1$-$C_4$ alkoxycarbonyl;

each Z independently represents hydrogen, halo, $C_1$-$C_4$ alkyl, $C_1$-$C_4$ alkoxy or —$CF_3$;

M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl; and n represents the integer 0, 1, 2 or 3;

and the herbicidally acceptable organic and inorganic salts thereof.

18. A method as defined in claim 17 wherein D is

19. A method as defined in claim 18 wherein R is hydrogen.

20. The method as defined in claim 19 wherein the active ingredient is 2-((1-ethoxyimino)propyl)-3-hydroxy-5-(3-(5-methylthio-2-pyridyloxy)phenyl)cyclohex-2-en-1-one.

21. The method as defined in claim 19 wherein the active ingredient is 2-((1-ethoxyimino)propyl)-3-hydroxy-5-(3-(5-methylsulfonyl-2-pyridyloxy)phenyl)-cyclohex-2-en-1-one.

22. A method as defined in claim 17 wherein D is

23. A method as defined in claim 17 wherein D is

24. A method as defined in claim 17 wherein D is

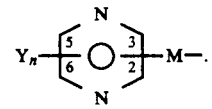

* * * * *